United States Patent [19]

Fayerman et al.

[11] Patent Number: 5,672,496
[45] Date of Patent: Sep. 30, 1997

[54] DNA SEQUENCES ENCODING PORCINE PANCREATIC CARBOXYPEPTIDASE B

[75] Inventors: Jeffrey T. Fayerman; David P. Greenen, both of Indianapolis; Charles L. Hershberger, Greenfield; Jeffrey L. Larson; Jane L. Sterner, both of Indianapolis, all of Ind.; Haichao Zhang, Park City, Ill.

[73] Assignee: Eli Lilly and Company, Indianapolis, Ind.

[21] Appl. No.: 696,139

[22] Filed: Aug. 13, 1996

Related U.S. Application Data

[63] Continuation of Ser. No. 153,258, Nov. 16, 1993, abandoned.

[51] Int. Cl.$^6$ ............................. C12N 15/57; C12N 9/48; C12N 1/19; C12N 15/81
[52] U.S. Cl. ................. 435/212; 435/69.1; 435/69.7; 435/69.8; 435/69.9; 435/71.1; 435/71.2; 435/252.3; 435/254.11; 435/254.23; 435/320.1; 435/938; 536/23.1; 536/23.2; 935/10; 935/14; 935/28; 935/37; 935/47; 935/48; 935/56; 935/68; 935/69; 935/72
[58] Field of Search ................... 536/23.1, 23.2; 435/69.1, 69.7, 69.8, 69.9, 71.1, 71.2, 212, 252.3, 254.11, 254.23, 320.1, 938; 935/10, 14, 28, 37, 47, 48, 56, 68, 69, 72

[56] References Cited

U.S. PATENT DOCUMENTS

| | | | |
|---|---|---|---|
| 5,102,789 | 4/1992 | Siegel et al. | 435/69.4 |
| 5,166,329 | 11/1992 | Cregg | 536/27 |
| 5,206,161 | 4/1993 | Drayna et al. | 435/212 |
| 5,330,901 | 7/1994 | Drevatt et al. | 435/69.6 |

OTHER PUBLICATIONS

Burgos, F. J., et al., *Biochemistry*, 30:4082–4089 (1991).

Eaton, D. L., J. Biol. Chem., 266 No. 32, 21,833–21,838 (1991).

Biotechnology, 9 1067–1072 (1991) Buckholz et al.

K.K. Yamamoto et al. "Isolation of a CDNA Encoding a Human Seron . . . " J. Biol. Chem. 267(4) 2575–2581 (Feb. 1992).

E. Clauser et al. "Structural Characterization of the Rat . . . " J. Biol. Chem. 263(33) 17837–17845 (Nov. 1988).

Sigma Biochemicals Catalog p. 212 (1992).

M. Coll et al. "Three–dimensional Structure of . . . " EMBO J. 10(1) 1–9 (Jan. 1991).

R.G. Buckholz et al. "Yeast Systems for the Commercial . . . " Bio/Technology 9: 1067–1072 (Nov. 1991).

Primary Examiner—Rebecca E. Prouty
Attorney, Agent, or Firm—Paul J. Gaylo; David E. Boone

[57] ABSTRACT

DNA encoding porcine Pro-carboxypeptidase B, vectors comprising the DNA and host cells transformed with the vectors are useful for production of porcine carboxypeptidase B

14 Claims, 9 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1215 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 1..1215

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| TAT | CAT | ATG | CAC | CAC | TCC | GGG | GAG | CAT | TTC | GAA | GGG | GAG | AAG | GTG | TTC | 48 |
| Tyr | His | Met | His | His | Ser | Gly | Glu | His | Phe | Glu | Gly | Glu | Lys | Val | Phe | |
| 1 | | | | 5 | | | | | 10 | | | | | 15 | | |
| CGT | GTC | AAT | GTT | GAA | GAT | GAA | AAT | GAC | ATC | AGC | TTA | CTC | CAT | GAG | TTG | 96 |
| Arg | Val | Asn | Val | Glu | Asp | Glu | Asn | Asp | Ile | Ser | Leu | Leu | His | Glu | Leu | |
| | | | 20 | | | | | 25 | | | | | 30 | | | |
| GCC | AGC | ACC | AGG | CAG | ATT | GAC | TTC | TGG | AAA | CCA | GAT | TCT | GTC | ACA | CAA | 144 |
| Ala | Ser | Thr | Arg | Gln | Ile | Asp | Phe | Trp | Lys | Pro | Asp | Ser | Val | Thr | Gln | |
| | | 35 | | | | | 40 | | | | | 45 | | | | |
| ATC | AAA | CCT | CAC | AGT | ACA | GTT | GAC | TTC | CGT | GTG | AAA | GCA | GAA | GAT | ATT | 192 |
| Ile | Lys | Pro | His | Ser | Thr | Val | Asp | Phe | Arg | Val | Lys | Ala | Glu | Asp | Ile | |
| | 50 | | | | 55 | | | | | 60 | | | | | | |
| TTG | GCT | GTG | GAA | GAC | TTT | CTG | GAG | CAG | AAT | GAA | CTA | CAA | TAT | GAG | GTA | 240 |
| Leu | Ala | Val | Glu | Asp | Phe | Leu | Glu | Gln | Asn | Glu | Leu | Gln | Tyr | Glu | Val | |
| 65 | | | | | 70 | | | | | 75 | | | | | 80 | |
| CTC | ATA | AAC | AAC | CTG | AGA | TCT | GTG | CTC | GAG | GCT | CAG | TTT | GAC | AGC | AGA | 288 |
| Leu | Ile | Asn | Asn | Leu | Arg | Ser | Val | Leu | Glu | Ala | Gln | Phe | Asp | Ser | Arg | |
| | | | | 85 | | | | | 90 | | | | | 95 | | |
| GTC | CGT | ACA | ACT | GGA | CAC | AGT | TAT | GAG | AAG | TAC | AAC | AAC | TGG | GAA | ACG | 336 |
| Val | Arg | Thr | Thr | Gly | His | Ser | Tyr | Glu | Lys | Tyr | Asn | Asn | Trp | Glu | Thr | |
| | | | 100 | | | | | 105 | | | | | 110 | | | |
| ATC | GAG | GCT | TGG | ACT | AAG | CAA | GTC | ACC | AGT | GAA | AAT | CCA | GAC | CTC | ATC | 384 |
| Ile | Glu | Ala | Trp | Thr | Lys | Gln | Val | Thr | Ser | Glu | Asn | Pro | Asp | Leu | Ile | |
| | | | 115 | | | | | 120 | | | | | 125 | | | |
| TCT | CGC | ACA | GCC | ATC | GGA | ACT | ACA | TTT | TTA | GGA | AAC | AAT | ATA | TAC | CTC | 432 |
| Ser | Arg | Thr | Ala | Ile | Gly | Thr | Thr | Phe | Leu | Gly | Asn | Asn | Ile | Tyr | Leu | |
| | 130 | | | | | 135 | | | | | 140 | | | | | |
| CTC | AAG | GTT | GGC | AAA | CCT | GGA | CCA | AAT | AAG | CCT | GCC | ATT | TTC | ATG | GAC | 480 |
| Leu | Lys | Val | Gly | Lys | Pro | Gly | Pro | Asn | Lys | Pro | Ala | Ile | Phe | Met | Asp | |
| 145 | | | | | 150 | | | | | 155 | | | | | 160 | |
| TGT | GGT | TTC | CAT | GCC | AGA | GAA | TGG | ATT | TCC | CAT | GCA | TTT | TGC | CAG | TGG | 528 |
| Cys | Gly | Phe | His | Ala | Arg | Glu | Trp | Ile | Ser | His | Ala | Phe | Cys | Gln | Trp | |
| | | | | 165 | | | | | 170 | | | | | 175 | | |
| TTT | GTG | AGA | GAG | GCT | GTT | CTC | ACC | TAT | GGA | TAT | GAG | AGT | CAC | ATG | ACA | 576 |
| Phe | Val | Arg | Glu | Ala | Val | Leu | Thr | Tyr | Gly | Tyr | Glu | Ser | His | Met | Thr | |
| | | | 180 | | | | | 185 | | | | | 190 | | | |
| GAA | TTC | CTC | AAC | AAG | CTA | GAC | TTT | TAT | GTC | TTG | CCT | GTG | CTC | AAT | ATT | 624 |
| Glu | Phe | Leu | Asn | Lys | Leu | Asp | Phe | Tyr | Val | Leu | Pro | Val | Leu | Asn | Ile | |
| | | 195 | | | | | 200 | | | | | 205 | | | | |
| GAT | GGC | TAC | ATC | TAC | ACC | TGG | ACC | AAG | AAC | CGA | ATG | TGG | AGA | AAG | ACC | 672 |
| Asp | Gly | Tyr | Ile | Tyr | Thr | Trp | Thr | Lys | Asn | Arg | Met | Trp | Arg | Lys | Thr | |
| | 210 | | | | | 215 | | | | | 220 | | | | | |
| CGC | TCT | ACC | AAT | GCT | GGA | ACT | ACC | TGC | ATT | GGC | ACA | GAC | CCC | AAC | AGA | 720 |
| Arg | Ser | Thr | Asn | Ala | Gly | Thr | Thr | Cys | Ile | Gly | Thr | Asp | Pro | Asn | Arg | |
| 225 | | | | | 230 | | | | | 235 | | | | | 240 | |
| AAT | TTT | GAT | GCT | GGG | TGG | TGC | ACA | ACT | GGA | GCC | TCT | ACA | GAC | CCC | TGC | 768 |
| Asn | Phe | Asp | Ala | Gly | Trp | Cys | Thr | Thr | Gly | Ala | Ser | Thr | Asp | Pro | Cys | |
| | | | | 245 | | | | | 250 | | | | | 255 | | |
| GAT | GAG | ACT | TAC | TGT | GGA | TCT | GCT | GCA | GAG | TCT | GAA | AAA | GAG | ACC | AAG | 816 |
| Asp | Glu | Thr | Tyr | Cys | Gly | Ser | Ala | Ala | Glu | Ser | Glu | Lys | Glu | Thr | Lys | |
| | | | 260 | | | | | 265 | | | | | 270 | | | |
| GCC | CTG | GCT | GAT | TTT | ATA | CGC | AAC | AAC | CTC | TCC | TCC | ATC | AAA | GCA | TAC | 864 |
| Ala | Leu | Ala | Asp | Phe | Ile | Arg | Asn | Asn | Leu | Ser | Ser | Ile | Lys | Ala | Tyr | |
| | | | 275 | | | | | 280 | | | | | 285 | | | |
| CTG | ACG | ATC | CAC | TCA | TAC | TCA | CAG | ATG | ATA | CTC | TAC | CCT | TAT | TCC | TAT | 912 |

```
         Leu  Thr  Ile  His  Ser  Tyr  Ser  Gln  Met  Ile  Leu  Tyr  Pro  Tyr  Ser  Tyr
              290                      295                           300

GAT  TAC  AAA  CTC  CCC  GAG  AAC  AAT  GCT  GAG  TTG  AAT  AAC  CTG  GCT  AAG          960
         Asp  Tyr  Lys  Leu  Pro  Glu  Asn  Asn  Ala  Glu  Leu  Asn  Asn  Leu  Ala  Lys
         305                      310                           315                320

GCT  GCC  GTG  AAA  GAA  CTT  GCT  ACA  CTG  TAT  GGC  ACC  AAG  TAC  ACA  TAC         1008
         Ala  Ala  Val  Lys  Glu  Leu  Ala  Thr  Leu  Tyr  Gly  Thr  Lys  Tyr  Thr  Tyr
                             325                      330                      335

GGC  CCA  GGA  GCT  ACA  ACA  ATC  TAT  CCT  GCT  GCT  GGG  GGC  TCT  GAT  GAC         1056
         Gly  Pro  Gly  Ala  Thr  Thr  Ile  Tyr  Pro  Ala  Ala  Gly  Gly  Ser  Asp  Asp
                        340                           345                      350

TGG  GCT  TAT  GAC  CAA  GGA  ATC  AAA  TAT  TCC  TTC  ACC  TTT  GAA  CTC  CGG         1104
         Trp  Ala  Tyr  Asp  Gln  Gly  Ile  Lys  Tyr  Ser  Phe  Thr  Phe  Glu  Leu  Arg
                   355                           360                 365

GAT  AAA  GGC  AGA  TAT  GGT  TTT  ATC  CTC  CCT  GAA  TCC  CAG  ATC  CAG  GCA         1152
         Asp  Lys  Gly  Arg  Tyr  Gly  Phe  Ile  Leu  Pro  Glu  Ser  Gln  Ile  Gln  Ala
              370                      375                      380

ACC  TGT  GAG  GAA  ACA  ATG  CTG  GCC  ATC  AAA  TAC  GTA  ACC  AAC  TAC  GTG         1200
         Thr  Cys  Glu  Glu  Thr  Met  Leu  Ala  Ile  Lys  Tyr  Val  Thr  Asn  Tyr  Val
         385                      390                      395                      400

CTG  GGC  CAC  CTG  TAA                                                                1215
         Leu  Gly  His  Leu
                        405
```

( 2 ) INFORMATION FOR SEQ ID NO:2:

( i ) SEQUENCE CHARACTERISTICS:
        ( A ) LENGTH: 404 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Tyr  His  Met  His  His  Ser  Gly  Glu  His  Phe  Glu  Gly  Glu  Lys  Val  Phe
 1                  5                       10                      15

Arg  Val  Asn  Val  Glu  Asp  Glu  Asn  Asp  Ile  Ser  Leu  Leu  His  Glu  Leu
               20                  25                           30

Ala  Ser  Thr  Arg  Gln  Ile  Asp  Phe  Trp  Lys  Pro  Asp  Ser  Val  Thr  Gln
          35                  40                       45

Ile  Lys  Pro  His  Ser  Thr  Val  Asp  Phe  Arg  Val  Lys  Ala  Glu  Asp  Ile
     50                  55                       60

Leu  Ala  Val  Glu  Asp  Phe  Leu  Glu  Gln  Asn  Glu  Leu  Gln  Tyr  Glu  Val
 65                      70                      75                       80

Leu  Ile  Asn  Asn  Leu  Arg  Ser  Val  Leu  Glu  Ala  Gln  Phe  Asp  Ser  Arg
               85                       90                      95

Val  Arg  Thr  Thr  Gly  His  Ser  Tyr  Glu  Lys  Tyr  Asn  Asn  Trp  Glu  Thr
               100                      105                     110

Ile  Glu  Ala  Trp  Thr  Lys  Gln  Val  Thr  Ser  Glu  Asn  Pro  Asp  Leu  Ile
          115                      120                     125

Ser  Arg  Thr  Ala  Ile  Gly  Thr  Thr  Phe  Leu  Gly  Asn  Asn  Ile  Tyr  Leu
     130                      135                      140

Leu  Lys  Val  Gly  Lys  Pro  Gly  Pro  Asn  Lys  Pro  Ala  Ile  Phe  Met  Asp
145                      150                      155                      160

Cys  Gly  Phe  His  Ala  Arg  Glu  Trp  Ile  Ser  His  Ala  Phe  Cys  Gln  Trp
               165                      170                      175

Phe  Val  Arg  Glu  Ala  Val  Leu  Thr  Tyr  Gly  Tyr  Glu  Ser  His  Met  Thr
               180                      185                      190

Glu  Phe  Leu  Asn  Lys  Leu  Asp  Phe  Tyr  Val  Leu  Pro  Val  Leu  Asn  Ile
```

|      |      |      | 195  |      |      |      | 200  |      |      |      |      | 205  |      |      |      |
|------|------|------|------|------|------|------|------|------|------|------|------|------|------|------|------|
| Asp  | Gly  | Tyr  | Ile  | Tyr  | Thr  | Trp  | Thr  | Lys  | Asn  | Arg  | Met  | Trp  | Arg  | Lys  | Thr  |
|      | 210  |      |      |      |      | 215  |      |      |      | 220  |      |      |      |      |      |
| Arg  | Ser  | Thr  | Asn  | Ala  | Gly  | Thr  | Thr  | Cys  | Ile  | Gly  | Thr  | Asp  | Pro  | Asn  | Arg  |
| 225  |      |      |      |      | 230  |      |      |      | 235  |      |      |      |      |      | 240  |
| Asn  | Phe  | Asp  | Ala  | Gly  | Trp  | Cys  | Thr  | Thr  | Gly  | Ala  | Ser  | Thr  | Asp  | Pro  | Cys  |
|      |      |      |      | 245  |      |      |      | 250  |      |      |      |      |      | 255  |      |
| Asp  | Glu  | Thr  | Tyr  | Cys  | Gly  | Ser  | Ala  | Ala  | Glu  | Ser  | Glu  | Lys  | Glu  | Thr  | Lys  |
|      |      |      | 260  |      |      |      |      | 265  |      |      |      |      | 270  |      |      |
| Ala  | Leu  | Ala  | Asp  | Phe  | Ile  | Arg  | Asn  | Asn  | Leu  | Ser  | Ser  | Ile  | Lys  | Ala  | Tyr  |
|      |      | 275  |      |      |      |      | 280  |      |      |      |      | 285  |      |      |      |
| Leu  | Thr  | Ile  | His  | Ser  | Tyr  | Ser  | Gln  | Met  | Ile  | Leu  | Tyr  | Pro  | Tyr  | Ser  | Tyr  |
|      | 290  |      |      |      |      | 295  |      |      |      |      | 300  |      |      |      |      |
| Asp  | Tyr  | Lys  | Leu  | Pro  | Glu  | Asn  | Asn  | Ala  | Glu  | Leu  | Asn  | Asn  | Leu  | Ala  | Lys  |
| 305  |      |      |      |      | 310  |      |      |      | 315  |      |      |      |      |      | 320  |
| Ala  | Ala  | Val  | Lys  | Glu  | Leu  | Ala  | Thr  | Leu  | Tyr  | Gly  | Thr  | Lys  | Tyr  | Thr  | Tyr  |
|      |      |      |      | 325  |      |      |      |      | 330  |      |      |      |      | 335  |      |
| Gly  | Pro  | Gly  | Ala  | Thr  | Thr  | Ile  | Tyr  | Pro  | Ala  | Ala  | Gly  | Gly  | Ser  | Asp  | Asp  |
|      |      |      | 340  |      |      |      |      | 345  |      |      |      |      | 350  |      |      |
| Trp  | Ala  | Tyr  | Asp  | Gln  | Gly  | Ile  | Lys  | Tyr  | Ser  | Phe  | Thr  | Phe  | Glu  | Leu  | Arg  |
|      |      | 355  |      |      |      |      | 360  |      |      |      | 365  |      |      |      |      |
| Asp  | Lys  | Gly  | Arg  | Tyr  | Gly  | Phe  | Ile  | Leu  | Pro  | Glu  | Ser  | Gln  | Ile  | Gln  | Ala  |
|      | 370  |      |      |      |      | 375  |      |      |      | 380  |      |      |      |      |      |
| Thr  | Cys  | Glu  | Glu  | Thr  | Met  | Leu  | Ala  | Ile  | Lys  | Tyr  | Val  | Thr  | Asn  | Tyr  | Val  |
| 385  |      |      |      |      | 390  |      |      |      | 395  |      |      |      |      |      | 400  |
| Leu  | Gly  | His  | Leu  |      |      |      |      |      |      |      |      |      |      |      |      |

( 2 ) INFORMATION FOR SEQ ID NO:3:

( i ) SEQUENCE CHARACTERISTICS:
        ( A ) LENGTH: 921 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..921

( x i ) SEQUENCE DESCRIPTION: SEQ ID NO:3:

| ACA | ACT | GGA | CAC | AGT | TAT | GAG | AAG | TAC | AAC | AAC | TGG | GAA | ACG | ATC | GAG | 48 |
| Thr | Thr | Gly | His | Ser | Tyr | Glu | Lys | Tyr | Asn | Asn | Trp | Glu | Thr | Ile | Glu | |
| 1 | | | | 5 | | | | | 10 | | | | | 15 | | |
| GCT | TGG | ACT | AAG | CAA | GTC | ACC | AGT | GAA | AAT | CCA | GAC | CTC | ATC | TCT | CGC | 96 |
| Ala | Trp | Thr | Lys | Gln | Val | Thr | Ser | Glu | Asn | Pro | Asp | Leu | Ile | Ser | Arg | |
| | | | 20 | | | | 25 | | | | | 30 | | | | |
| ACA | GCC | ATC | GGA | ACT | ACA | TTT | TTA | GGA | AAC | AAT | ATA | TAC | CTC | CTC | AAG | 144 |
| Thr | Ala | Ile | Gly | Thr | Thr | Phe | Leu | Gly | Asn | Asn | Ile | Tyr | Leu | Leu | Lys | |
| | | 35 | | | | 40 | | | | | 45 | | | | | |
| GTT | GGC | AAA | CCT | GGA | CCA | AAT | AAG | CCT | GCC | ATT | TTC | ATG | GAC | TGT | GGT | 192 |
| Val | Gly | Lys | Pro | Gly | Pro | Asn | Lys | Pro | Ala | Ile | Phe | Met | Asp | Cys | Gly | |
| | 50 | | | | 55 | | | | | 60 | | | | | | |
| TTC | CAT | GCC | AGA | GAA | TGG | ATT | TCC | CAT | GCA | TTT | TGC | CAG | TGG | TTT | GTG | 240 |
| Phe | His | Ala | Arg | Glu | Trp | Ile | Ser | His | Ala | Phe | Cys | Gln | Trp | Phe | Val | |
| 65 | | | | 70 | | | | 75 | | | | | | 80 | | |
| AGA | GAG | GCT | GTT | CTC | ACC | TAT | GGA | TAT | GAG | AGT | CAC | ATG | ACA | GAA | TTC | 288 |
| Arg | Glu | Ala | Val | Leu | Thr | Tyr | Gly | Tyr | Glu | Ser | His | Met | Thr | Glu | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| CTC | AAC | AAG | CTA | GAC | TTT | TAT | GTC | TTG | CCT | GTG | CTC | AAT | ATT | GAT | GGC | 336 |
| Leu | Asn | Lys | Leu | Asp | Phe | Tyr | Val | Leu | Pro | Val | Leu | Asn | Ile | Asp | Gly | |
| | | | 100 | | | | 105 | | | | | | 110 | | | |
| TAC | ATC | TAC | ACC | TGG | ACC | AAG | AAC | CGA | ATG | TGG | AGA | AAG | ACC | CGC | TCT | 384 |
| Tyr | Ile | Tyr | Thr | Trp | Thr | Lys | Asn | Arg | Met | Trp | Arg | Lys | Thr | Arg | Ser | |
| | | 115 | | | | | 120 | | | | | 125 | | | | |
| ACC | AAT | GCT | GGA | ACT | ACC | TGC | ATT | GGC | ACA | GAC | CCC | AAC | AGA | AAT | TTT | 432 |
| Thr | Asn | Ala | Gly | Thr | Thr | Cys | Ile | Gly | Thr | Asp | Pro | Asn | Arg | Asn | Phe | |
| | 130 | | | | | 135 | | | | | 140 | | | | | |
| GAT | GCT | GGG | TGG | TGC | ACA | ACT | GGA | GCC | TCT | ACA | GAC | CCC | TGC | GAT | GAG | 480 |
| Asp | Ala | Gly | Trp | Cys | Thr | Thr | Gly | Ala | Ser | Thr | Asp | Pro | Cys | Asp | Glu | |
| 145 | | | | | 150 | | | | | 155 | | | | | 160 | |
| ACT | TAC | TGT | GGA | TCT | GCT | GCA | GAG | TCT | GAA | AAA | GAG | ACC | AAG | GCC | CTG | 528 |
| Thr | Tyr | Cys | Gly | Ser | Ala | Ala | Glu | Ser | Glu | Lys | Glu | Thr | Lys | Ala | Leu | |
| | | | | 165 | | | | | 170 | | | | | 175 | | |
| GCT | GAT | TTT | ATA | CGC | AAC | AAC | CTC | TCC | TCC | ATC | AAA | GCA | TAC | CTG | ACG | 576 |
| Ala | Asp | Phe | Ile | Arg | Asn | Asn | Leu | Ser | Ser | Ile | Lys | Ala | Tyr | Leu | Thr | |
| | | | 180 | | | | | 185 | | | | | 190 | | | |
| ATC | CAC | TCA | TAC | TCA | CAG | ATG | ATA | CTC | TAC | CCT | TAT | TCC | TAT | GAT | TAC | 624 |
| Ile | His | Ser | Tyr | Ser | Gln | Met | Ile | Leu | Tyr | Pro | Tyr | Ser | Tyr | Asp | Tyr | |
| | | 195 | | | | | 200 | | | | | 205 | | | | |
| AAA | CTC | CCC | GAG | AAC | AAT | GCT | GAG | TTG | AAT | AAC | CTG | GCT | AAG | GCT | GCC | 672 |
| Lys | Leu | Pro | Glu | Asn | Asn | Ala | Glu | Leu | Asn | Asn | Leu | Ala | Lys | Ala | Ala | |
| | 210 | | | | | 215 | | | | | 220 | | | | | |
| GTG | AAA | GAA | CTT | GCT | ACA | CTG | TAT | GGC | ACC | AAG | TAC | ACA | TAC | GGC | CCA | 720 |
| Val | Lys | Glu | Leu | Ala | Thr | Leu | Tyr | Gly | Thr | Lys | Tyr | Thr | Tyr | Gly | Pro | |
| 225 | | | | | 230 | | | | | 235 | | | | | 240 | |
| GGA | GCT | ACA | ACA | ATC | TAT | CCT | GCT | GCT | GGG | GGC | TCT | GAT | GAC | TGG | GCT | 768 |
| Gly | Ala | Thr | Thr | Ile | Tyr | Pro | Ala | Ala | Gly | Gly | Ser | Asp | Asp | Trp | Ala | |
| | | | | 245 | | | | | 250 | | | | | 255 | | |
| TAT | GAC | CAA | GGA | ATC | AAA | TAT | TCC | TTC | ACC | TTT | GAA | CTC | CGG | GAT | AAA | 816 |
| Tyr | Asp | Gln | Gly | Ile | Lys | Tyr | Ser | Phe | Thr | Phe | Glu | Leu | Arg | Asp | Lys | |
| | | | 260 | | | | | 265 | | | | | 270 | | | |
| GGC | AGA | TAT | GGT | TTT | ATC | CTC | CCT | GAA | TCC | CAG | ATC | CAG | GCA | ACC | TGT | 864 |
| Gly | Arg | Tyr | Gly | Phe | Ile | Leu | Pro | Glu | Ser | Gln | Ile | Gln | Ala | Thr | Cys | |
| | | 275 | | | | | 280 | | | | | 285 | | | | |
| GAG | GAA | ACA | ATG | CTG | GCC | ATC | AAA | TAC | GTA | ACC | AAC | TAC | GTG | CTG | GGC | 912 |
| Glu | Glu | Thr | Met | Leu | Ala | Ile | Lys | Tyr | Val | Thr | Asn | Tyr | Val | Leu | Gly | |
| | 290 | | | | | 295 | | | | | 300 | | | | | |
| CAC | CTG | TAA | | | | | | | | | | | | | | 921 |
| His | Leu | | | | | | | | | | | | | | | |
| 305 | | | | | | | | | | | | | | | | |

( 2 ) INFORMATION FOR SEQ ID NO:4:

( i ) SEQUENCE CHARACTERISTICS:
        ( A ) LENGTH: 306 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Thr | Thr | Gly | His | Ser | Tyr | Glu | Lys | Tyr | Asn | Asn | Trp | Glu | Thr | Ile | Glu |
| 1 | | | | 5 | | | | | 10 | | | | | 15 | |
| Ala | Trp | Thr | Lys | Gln | Val | Thr | Ser | Glu | Asn | Pro | Asp | Leu | Ile | Ser | Arg |
| | | | 20 | | | | 25 | | | | | 30 | | | |
| Thr | Ala | Ile | Gly | Thr | Thr | Phe | Leu | Gly | Asn | Asn | Ile | Tyr | Leu | Leu | Lys |
| | | | 35 | | | | 40 | | | | | 45 | | | |
| Val | Gly | Lys | Pro | Gly | Pro | Asn | Lys | Pro | Ala | Ile | Phe | Met | Asp | Cys | Gly |
| | 50 | | | | | 55 | | | | | 60 | | | | |

| | | | | | | | | | | | | | | |
|---|---|---|---|---|---|---|---|---|---|---|---|---|---|---|
| Phe | His | Ala | Arg | Glu | Trp | Ile | Ser | His | Ala | Phe | Cys | Gln | Trp | Phe | Val |
| 65 | | | | 70 | | | | | 75 | | | | | 80 |

Phe His Ala Arg Glu Trp Ile Ser His Ala Phe Cys Gln Trp Phe Val
65                    70                    75                    80

Arg Glu Ala Val Leu Thr Tyr Gly Tyr Glu Ser His Met Thr Glu Phe
                    85                    90                    95

Leu Asn Lys Leu Asp Phe Tyr Val Leu Pro Val Leu Asn Ile Asp Gly
            100                   105                   110

Tyr Ile Tyr Thr Trp Thr Lys Asn Arg Met Trp Arg Lys Thr Arg Ser
        115                   120                   125

Thr Asn Ala Gly Thr Thr Cys Ile Gly Thr Asp Pro Asn Arg Asn Phe
    130                   135                   140

Asp Ala Gly Trp Cys Thr Thr Gly Ala Ser Thr Asp Pro Cys Asp Glu
145                   150                   155                   160

Thr Tyr Cys Gly Ser Ala Ala Glu Ser Glu Lys Glu Thr Lys Ala Leu
                165                   170                   175

Ala Asp Phe Ile Arg Asn Asn Leu Ser Ser Ile Lys Ala Tyr Leu Thr
            180                   185                   190

Ile His Ser Tyr Ser Gln Met Ile Leu Tyr Pro Tyr Ser Tyr Asp Tyr
        195                   200                   205

Lys Leu Pro Glu Asn Asn Ala Glu Leu Asn Asn Leu Ala Lys Ala Ala
    210                   215                   220

Val Lys Glu Leu Ala Thr Leu Tyr Gly Thr Lys Tyr Thr Tyr Gly Pro
225                   230                   235                   240

Gly Ala Thr Thr Ile Tyr Pro Ala Ala Gly Gly Ser Asp Asp Trp Ala
                245                   250                   255

Tyr Asp Gln Gly Ile Lys Tyr Ser Phe Thr Phe Glu Leu Arg Asp Lys
            260                   265                   270

Gly Arg Tyr Gly Phe Ile Leu Pro Glu Ser Gln Ile Gln Ala Thr Cys
        275                   280                   285

Glu Glu Thr Met Leu Ala Ile Lys Tyr Val Thr Asn Tyr Val Leu Gly
    290                   295                   300

His Leu
305

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TACTAGTTGC A                            11

( 2 ) INFORMATION FOR SEQ ID NO:6:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

ACTAGTATGC A                            11

DNA SEQUENCES ENCODING PORCINE PANCREATIC CARBOXYPEPTIDASE B

This application is a continuation of application Ser. No. 08/153,258, filed on Nov. 16, 1993 now abandoned.

BACKGROUND OF THE INVENTION

The family of enzymes known as carboxypeptidases is well known in the art. The present invention is directed to cDNA molecules encoding porcine carboxypeptidase B, vectors comprising the cDNA, host cells transformed with the vectors to generate carboxypeptidase B expression systems and methods of utilizing the expression vectors for production of carboxypeptidase B.

The term "carboxypeptidase B" generically refers to metallo-exopeptidases which preferentially cleave basic residues from the carboxy terminus of proteins. The amino acid sequences of rat, human and bovine tissue procarboxypeptidases are similar. See Eaton, D. L., *J. Biol. Chem.* 266, No. 32, 21833–21838, 1991.

A variety of recombinant DNA expression systems are sutiable for expression of polypeptide products such as the carboxypeptidase B and its enzymatically active varients which are taught in the present invention. *Pichia pastoris* is the preferred expression system, but bacterial expression systems such as *E. coli*, insect expression systems such as the Baculovirus expression systems and numerous other expression systems including mammalian expression systems are well known in the art to be amenable to expression of myriad polypeptide products of interest.

*Pichia pastoris* is a yeast and thus affords advantages as a host cell for production of genetically engineered products of interest. The use of bacterial expression systems for production of genetically engineered products of interest often requires that the product be recovered from the bacteria in the form of a granule, which must be solubilized and the material released therefrom must then be folded to generate a molecule having the tertiary and quartenary structure required for biological activity. Proteins produced in Pichia do not require solubilization and folding. Signal peptides can be genetically engineered to provide a Pichia expression system which will secrete the desired product in biologically active form into the culture medium.

Pichia expression systems are well known in the art and have been utilized for production of human serum albumin, human epidermal growth factor, hepatitis antigens, bovine lysozyme, human lysozyme, human insulin-like growth factor I, aprotin, interleukin 2, streptokinase, human tissue plasminogen activating factor, the gp120 antigen of HIV, the gp120 antigen of SIV, pertactin, tetanus C, murine epidermal growth factor, and human tissue necrosis factor. Buckholz, G. B. and Gleeson, M. A. G., *Biotechnology* 9, 1067–1072, (1991).

SUMMARY OF INVENTION

The present invention provides cDNA molecules encoding porcine procarboxypeptidase B, Tyr-His-Met-pro-porcine pancreatic carboxypeptidase B, vectors comprising the cDNAs, *Pichia pastoris* cells transformed with the vectors to generate carboxypeptidase B expression systems and methods of utilizing the *Pichia pastoris* expression systems for production of the porcine carboxypeptidase B and N-terminal extended equivalents thereof. Bacterial, insect, and mammalian expression systems are also amenable to production of the enzymes of the present invention and are included within the scope of the invention.

DETAILED DESCRIPTION

Figure 1:
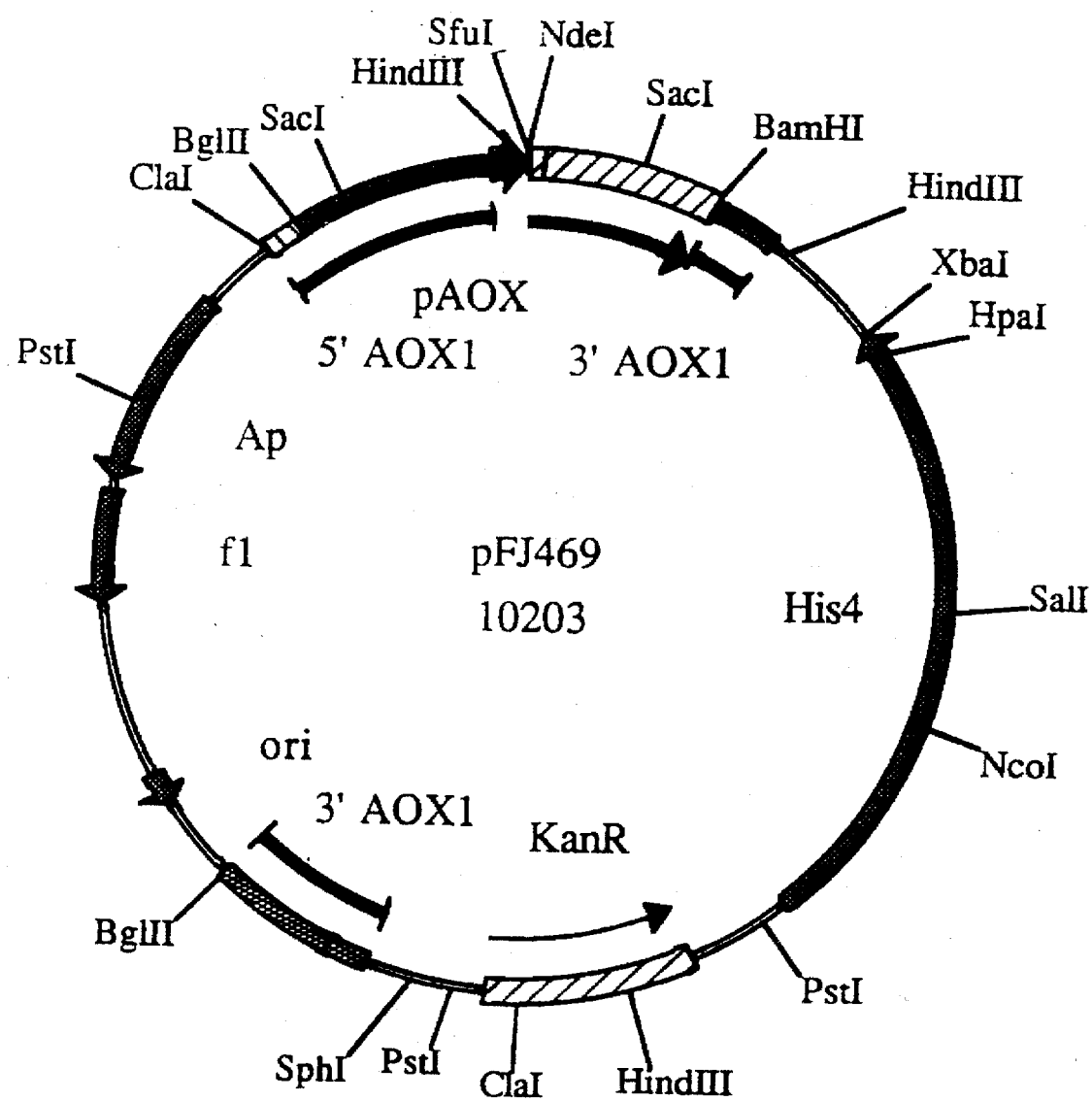
FIG. 1 is a restriction site and function map of plasmid pFJ469.

The present invention provides recombinant DNA expression vectors and host cells transformed therewith for the expression of porcine procarboxypeptidase B and porcine Tyr-His-Met-procarboxypeptidase B.

A double-stranded cDNA sequence of the present invention which encodes Tyr-His-Met-porcine procarboxypeptidase as well as the amino acid sequence encoded thereby is provided below as Formula I. The single stranded DNA sequence corresponding to the sense strand of Formula I is also provided as Sequence ID 1. The amino acid sequence of Formula 1 is provided as Sequence ID 2. Formula 1 is provided to supplement the Sequence ID section because it provides a convenient reference to the restriction endonuclease sites utilized in the construction of the vectors of the present invention while simultaneously providing the amino acid sequences encoded by the respective codons.

Formula 1

```
            N
            d
            e
            I
    TATCATATGCACCACTCCGGGGAGCATTTCGAAGGGGAGAAGGTGTTCCGTGTCAATGTT
1   ----------+----------+----------+----------+----------+----------+
60
    ATAGTATACGTGGTGAGGCCCCTCGTAAAGCTTCCCCTCTTCCACAAGGCACAGTTACAA
    Tyr His Met His His Ser Gly Glu His Phe Glu Gly Glu Lys Val Phe Arg Val Asn Val
```

-continued

Formula 1

```
        GAAGATGAAAATGACATCAGCTTACTCCATGAGTTGGCCAGCACCAGGCAGATTGACTTC
    61  ---------+---------+---------+---------+---------+---------+
   120
        CTTCTACTTTTACTGTAGTCGAATGAGGTACTCAACCGGTCGTGGTCCGTCTAACTGAAG

Glu Asp Glu Asn Asp Ile Ser Leu Leu His Glu Leu Ala Ser Thr Arg Gln Ile Asp Phe

TGGAAACCAGATTCTGTCACACAAATCAAACCTCACAGTACAGTTGACTTCCGTGTGAAA
   121  ---------+---------+---------+---------+---------+---------+
   180
        ACCTTTGGTCTAAGACAGTGTGTTTAGTTTGGAGTGTCATGTCAACTGAAGGCACACTTT

Trp Lys Pro Asp Ser Val Thr Gln Ile Lys Pro His Ser Thr Val Asp Phe Arg Val Lys

GCAGAAGATATTTTGGCTGTGGAAGACTTTCTGGAGCAGAATGAACTACAATATGAGGTA
   181  ---------+---------+---------+---------+---------+---------+
   240
        CGTCTTCTATAAAACCGACACCTTCTGAAAGACCTCGTCTTACTTGATGTTATACTCCAT

Ala Glu Asp Ile Leu Ala Val Glu Asp Phe Leu Glu Gln Asn Glu Leu Gln Tyr Glu Val

B
                            g       X
                            l       h
                            I       o
                            I       I
        CTCATAAACAACCTGAGATCTGTGCTCGAGGCTCAGTTTGACAGCAGAGTCCGTACAACT
   241  ---------+---------+---------+---------+---------+---------+
   300
        GAGTATTTGTTGGACTCTAGACACGAGCTCCGAGTCAAACTGTCGTCTCAGGCATGTTGA

Leu Ile Asn Asn Leu Arg Ser Val Leu Glu Ala Gln Phe Asp Ser Arg Val Arg Thr Thr

GGACACAGTTATGAGAAGTACAACAACTGGGAAACGATCGAGGCTTGGACTAAGCAAGTC
   301  ---------+---------+---------+---------+---------+---------+
   360
        CCTGTGTCAATACTCTTCATGTTGTTGACCCTTTGCTAGCTCCGAACCTGATTCGTTCAG

Gly His Ser Tyr Glu Lys Tyr Asn Asn Trp Glu Thr Ile Glu Ala Trp Thr Lys Gln Val

ACCAGTGAAAATCCAGACCTCATCTCTCGCACAGCCATCGGAACTACATTTTTAGGAAAC
   361  ---------+---------+---------+---------+---------+---------+
   420
        TGGTCACTTTTAGGTCTGGAGTAGAGAGCGTGTCGGTAGCCTTGATGTAAAAATCCTTTG

Thr Ser Glu Asn Pro Asp Leu Ile Ser Arg Thr Ala Ile Gly Thr Thr Phe Leu Gly Asn

AATATATACCTCCTCAAGGTTGGCAAACCTGGACCAAATAAGCCTGCCATTTTCATGGAC
   421  ---------+---------+---------+---------+---------+---------+
   480
        TTATATATGGAGGAGTTCCAACCGTTTGGACCTGGTTTATTCGGACGGTAAAAGTACCTG

Asn Ile Tyr Leu Leu Lys Val Gly Lys Pro Gly Pro Asn Lys Pro Ala Ile Phe Met Asp

TGTGGTTTCCATGCCAGAGAATGGATTTCCCATGCATTTTGCCAGTGGTTTGTGAGAGAG
   481  ---------+---------+---------+---------+---------+---------+
   540
        ACACCAAAGGTACGGTCTCTTACCTAAAGGGTACGTAAAACGGTCACCAAACACTCTCTC

Cys Gly Phe His Ala Arg Glu Trp Ile Ser His Ala Phe Cys Gln Trp Phe Val Arg Glu

GCTGTTCTCACCTATGGATATGAGAGTCACATGACAGAATTCCTCAACAAGCTAGACTTT
   541  ---------+---------+---------+---------+---------+---------+
   600
        CGACAAGAGTGGATACCTATACTCTCAGTGTACTGTCTTAAGGAGTTGTTCGATCTGAAA

Ala Val Leu Thr Tyr Gly Tyr Glu Ser His Met Thr Glu Phe Leu Asn Lys Leu Asp Phe

TATGTCTTGCCTGTGCTCAATATTGATGGCTACATCTACACCTGGACCAAGAACCGAATG
   601  ---------+---------+---------+---------+---------+---------+
   660
        ATACAGAACGGACACGAGTTATAACTACCGATGTAGATGTGGACCTGGTTCTTGGCTTAC

Tyr Val Leu Pro Val Leu Asn Ile Asp Gly Tyr Ile Tyr Thr Trp Thr Lys Asn Arg Met
```

-continued

Formula 1

```
         TGGAGAAAGACCCGCTCTACCAATGCTGGAACTACCTGCATTGGCACAGACCCCAACAGA
   661   ---------+---------+---------+---------+---------+---------+
   720
         ACCTCTTTCTGGGCGAGATGGTTACGACCTTGATGGACGTAACCGTGTCTGGGGTTGTCT

Trp Arg Lys Thr Arg Ser Thr Asn Ala Gly Thr Thr Cys Ile Gly Thr Asp Pro Asn Arg

AATTTTGATGCTGGGTGGTGCACAACTGGAGCCTCTACAGACCCCTGCGATGAGACTTAC
   721   ---------+---------+---------+---------+---------+---------+
   780
         TTAAAACTACGACCCACCACGTGTTGACCTCGGAGATGTCTGGGGACGCTACTCTGAATG

Asn Phe Asp Ala Gly Trp Cys Thr Thr Gly Ala Ser Thr Asp Pro Cys Asp Glu Thr Tyr

P
                                           s
                                           t
                                           I
         TGTGGATCTGCTGCAGAGTCTGAAAAAGAGACCAAGGCCCTGGCTGATTTTATACGCAAC
   781   ---------+---------+---------+---------+---------+---------+
   840
         ACACCTAGACGACGTCTCAGACTTTTTCTCTGGTTCCGGGACCGACTAAAATATGCGTTG

Cys Gly Ser Ala Ala Glu Ser Glu Lys Glu Thr Lys Ala Leu Ala Asp Phe Ile Arg Asn

AACCTCTCCTCCATCAAAGCATACCTGACGATCCACTCATACTCACAGATGATACTCTAC
   841   ---------+---------+---------+---------+---------+---------+
   900
         TTGGAGAGGAGGTAGTTTCGTATGGACTGCTAGGTGAGTATGAGTGTCTACTATGAGATG

Asn Leu Ser Ser Ile Lys Ala Tyr Leu Thr Ile His Ser Tyr Ser Gln Met Ile Leu Tyr

CCTTATTCCTATGATTACAAACTCCCCGAGAACAATGCTGAGTTGAATAACCTGGCTAAG
   901   ---------+---------+---------+---------+---------+---------+
   960
         GGAATAAGGATACTAATGTTTGAGGGGCTCTTGTTACGACTCAACTTATTGGACCGATTC

Pro Tyr Ser Tyr Asp Tyr Lys Leu Pro Glu Asn Asn Ala Glu Leu Asn Asn Leu Ala Lys

GCTGCCGTGAAAGAACTTGCTACACTGTATGGCACCAAGTACACATACGGCCCAGGAGCT
   961   ---------+---------+---------+---------+---------+---------+
  1020
         CGACGGCACTTTCTTGAACGATGTGACATACCGTGGTTCATGTGTATGCCGGGTCCTCGA

Ala Ala Val Lys Glu Leu Ala Thr Leu Tyr Gly Thr Lys Tyr Thr Tyr Gly Pro Gly Ala

ACAACAATCTATCCTGCTGCTGGGGGCTCTGATGACTGGGCTTATGACCAAGGAATCAAA
  1021   ---------+---------+---------+---------+---------+---------+
  1080
         TGTTGTTAGATAGGACGACGACCCCCGAGACTACTGACCCGAATACTGGTTCCTTAGTTT

Thr Thr Ile Tyr Pro Ala Ala Gly Gly Ser Asp Asp Trp Ala Tyr Asp Gln Gly Ile Lys

TATTCCTTCACCTTTGAACTCCGGGATAAAGGCAGATATGGTTTTATCCTCCCTGAATCC
  1081   ---------+---------+---------+---------+---------+---------+
  1140
         ATAAGGAAGTGGAAACTTGAGGCCCTATTTCCGTCTATACCAAAATAGGAGGGACTTAGG

Tyr Ser Phe Thr Phe Glu Leu Arg Asp Lys Gly Arg Tyr Gly Phe Ile Leu Pro Glu Ser

CAGATCCAGGCAACCTGTGAGGAAACAATGCTGGCCATCAAATACGTAACCAACTACGTG
  1141   ---------+---------+---------+---------+---------+---------+
  1200
         GTCTAGGTCCGTTGGACACTCCTTTGTTACGACCGGTAGTTTATGCATTGGTTGATGCAC

Gln Ile Gln Ala Thr Cys Glu Glu Thr Met Leu Ala Ile Lys Tyr Val Thr Asn Tyr Val

CTGGGCCACCTGTAA
  1201   ---------+----- 1215
         GACCCGGTGGACATT

Leu Gly His Leu End
```

The DNA sequence and corresponding amino acid sequence of Formula I represents the cDNA sequence encoding porcine procarboxypeptidase B which has an N-terminal extension of Tyr-His-Met. The procarboxypeptidase B and N-terminal extended variants thereof are readily converted to carboxypeptidase B by treatment with trypsin, which cleaves the polypeptide of Formula 1 between amino acids 98 and 99. The coding sequence for porcine carboxypeptidase is provided as Sequence ID 3 and the corresponding translation product is designated Sequence ID 4.

Plasmid pFJ474 contains the coding sequence for Tyr-His-Met-porcine procarboxypeptidase B (Formula I). Plasmid pFJ474 has been deposited in the Northern Regional Research Laboratory (NRRL) Peoria, Ill., where it will be publicly available under the accession number NRRL B-21032 upon issuance of the present application.

Plasmid pFJ489 contains the coding sequence for porcine procarboxypeptidase B (Formula I minus the first 3 codons, which encode Y, H, and M, respectively). Plasmid pFJ489 has been deposited in the Northern Regional Research Laboratory (NRRL) Peoria, Ill., where it will be publicly available under the accession number NRRL B-21028 upon issuance of the present application.

The preferred host cells for expression of the carboxypeptidase Bs of the present invention are Pichia pastoris, hereinafter abbreviated P. pastoris. Bacterial, insect, and mammalian expression systems are well known in the art and are also amenable to production of the enzymes of the present invention and are included within the scope of the invention.

The utility of P. pastoris for expression of polypeptide products of interest is well known in the art. U.S. Pat. Nos. 5,102,789, 5,004,688, 4,882,279, 5,032,516 provide background information on P. pastoris as well as detail on numerous vectors of use in the genetic engineering of Pichia. The contents of the aforementioned patents are herein incorporated by reference. An especially preferred strain of P. pastoris is GTS 115. P. pastoris GTS115 was deposited in the Northern Regional Research Laboratory (NRRL) Peoria, Ill., on Aug. 31, 1984. P. pastoris GTS 115 is available from the NRRL under the accession number Y15851 P. pastoris GTS115 was generated by nitrosoguanadine mutagenesis of NRRL Y-11430 and contains a defect in histidinol dehydrogenase activity, which is coded by the gene HIS4. GTS115 grows on complex media such as YPD and on minimal medias such as MMH, MDH or MGYH which have been supplemented with histidine. The defect in HIS4 provides a convenient selection means for vectors comprising the HIS4 gene derived from Pichia or other yeast. GTS115 is sometimes referred to in the literature as GS115.

Numerous other strains of Pichia pastoris are publicly available from sources including the NRRL and the American Type Culture Collection (ATCC), 12301 Parklawn Drive, Rockville, Md. For example, the 1990 ATCC Catalog of Yeasts lists 8 strains of P. pastoris. While the GTS115 strain of P. pastoris is preferred, the other strains of P. pastoris are compatable with the vectors of the present invention and thus are within the scope of the invention.

The genetic engineering of P. pastoris has benefitted from the number of regulatory units and selectable markers which are known in the art to function in yeasts. The vectors taught and claimed herein utilize some elements known in the art. Vectors have been deposited as a convenient source for many of the promoters, signal peptides, antibiotic resistance markers, coding sequences, integration functions, and other elements used to construct the vectors of the invention. The deposited materials are summarized in Table I.

TABLE I

| Host cell/vector | NRRL Accession Number | Figure Number |
| --- | --- | --- |
| E. coli RV308/pFJ469 | B-21025 | 1 |
| E. coli DH5α/pLGD27 | B-21027 | 2 |
| E. coli 294/pFJ489 | B-21028 | 3 |
| E. coli 294/pLGD23 | B-21029 | 4 |
| E. coli 294/pFJ457 | B-21030 | 5 |
| E. coli 294/pLGD36 | B-21031 | 6 |
| E. coli RV308/pFJ474 | B-21032 | 7 |
| E. coli RV308/pFJ471 | B-21033 | 8 |
| E. coli 294/pLGD20 | B-21034 | 9 |

The vectors of the present invention comprise both autonomously replicating and integrating vectors. The integrative vectors utilize the 5' AOX1 and the 3'AOX1 sequences for homologous recombination into the P. pastoris chromosome. AOX refers to the alcohol oxidase genes of P. pastoris and the 5' and 3' designations delineate whether these sequences are upstream or downstream of the alcohol oxidase gene, AOX1, on the P. pastoris chromosome. AOX2 is the designation for the second alcohol oxidase gene of the P. pastoris genome and will not be referred to further because it is not utilized for expression in the illustrative vectors of the present invention and its flanking regions are not utilized for recombination. U.S. Pat. No. 5,166,329 discusses the alcohol oxidase genes of P. pastoris and their regulatory units. Skilled artisans will realize that AOX2 would also be useful for expression, but AOX1 is the preferred methanol inducable promoter for purposes of the present invention. Site selective insertion into the P. pastoris chromosome via the aforementioned alcohol oxidase flanking sequences is taught in U.S. Pat. No. 4,882,279, the contents of which are herein incorporated by reference. Skilled artisans will realize that the 5' and 3' AOX1 sequences allow site specific integration via homologous recombination into the host chromosome. Reference to the Examples and Figures indicates that the recombination event can occur for many of the vectors by two different recombinations however it will be understood that unless the HIS4 sequence is present on the fragment which recombines into the Pichia chromosome it will not be detected due to the use of histadinol deficient media used for selection in histadine dehydrogenase deficient strains such as GTS115. It will also be understood that when strains of Pichia which are not histidine auxotrophs are used recombinants of both varieties will result. The PARS1 sequence, which is well known in the art, is used for the construction of autonomously replicating vectors. The integrative forms of the vectors are preferred.

Many of the vectors of the present invention comprise elements which allow replication and selection in E. coli. The ampicillin (Amp$^R$ or Ap) resistance marker is useful for selection in E. coli. A kanamycin resistance gene (KanR) allows selection in E. coli.

Figure 4:
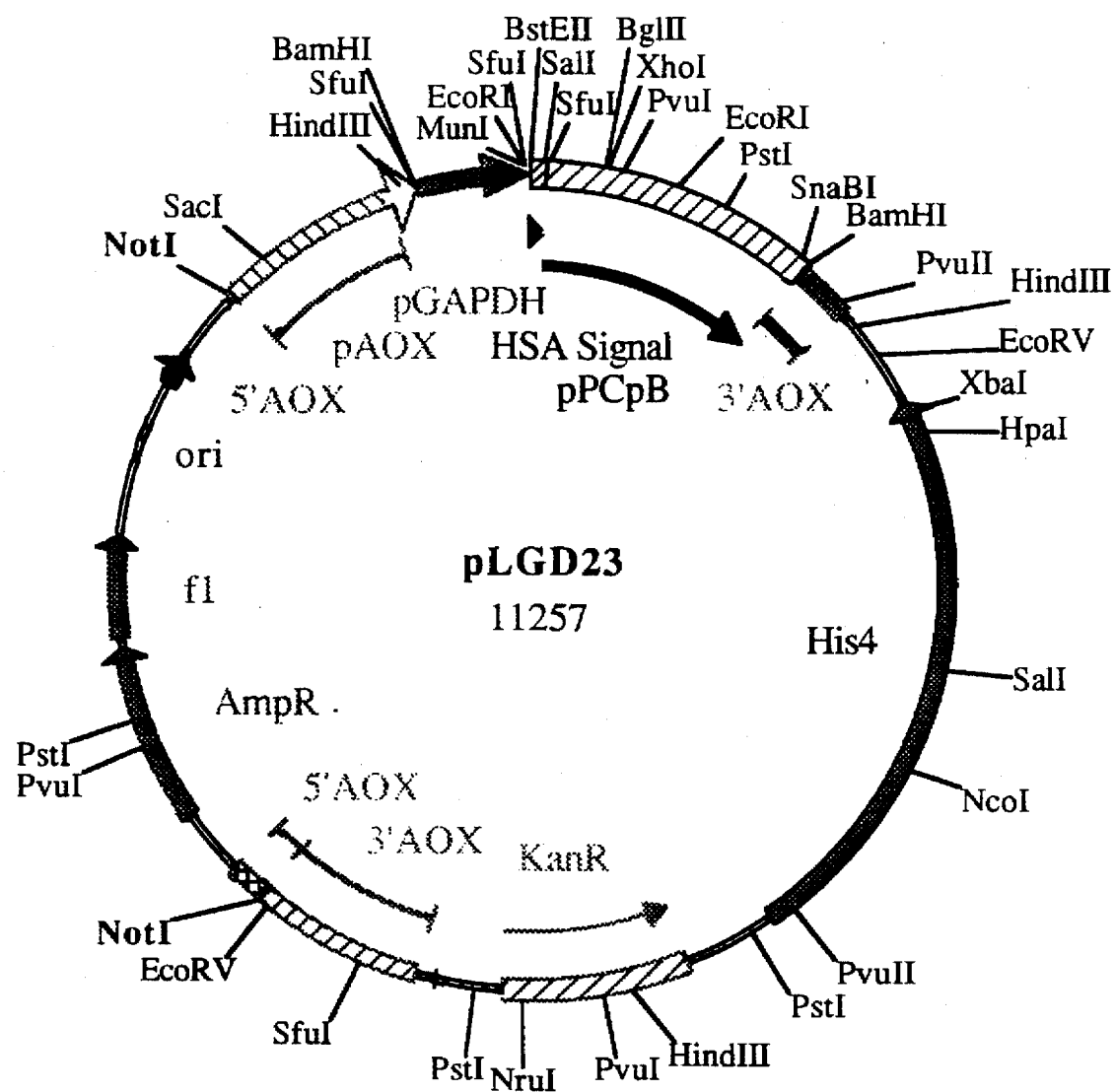
FIG. 4 is a restriciton site and function map of plasmid pLGD23. pLGD23 contains approximately 11,257 base pairs.
Figure 5:
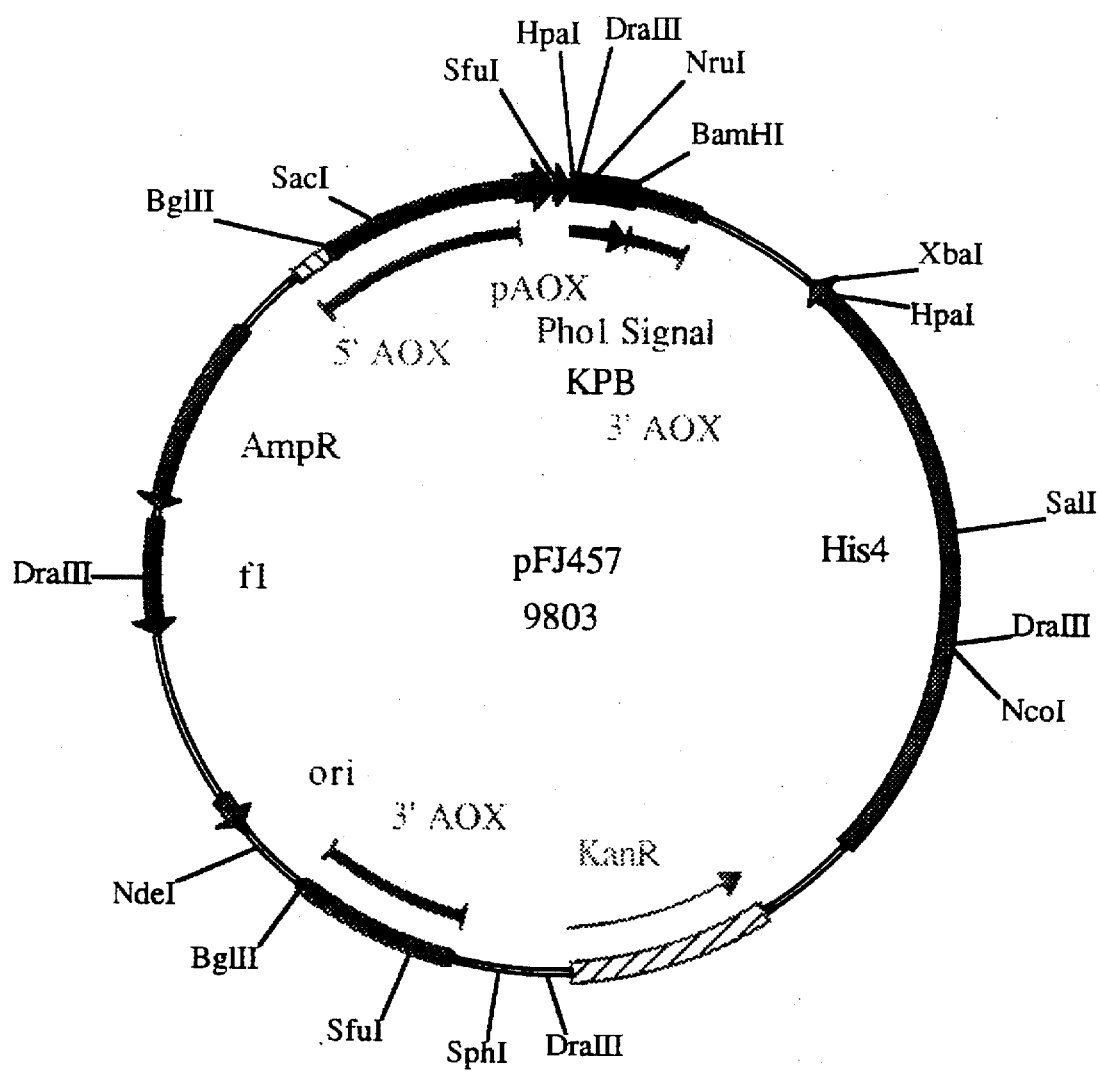
FIG. 5 is a restriction site and function map of plasmid pFJ457. pFJ457 contains approximately 9,803 base pairs.
Figure 9:
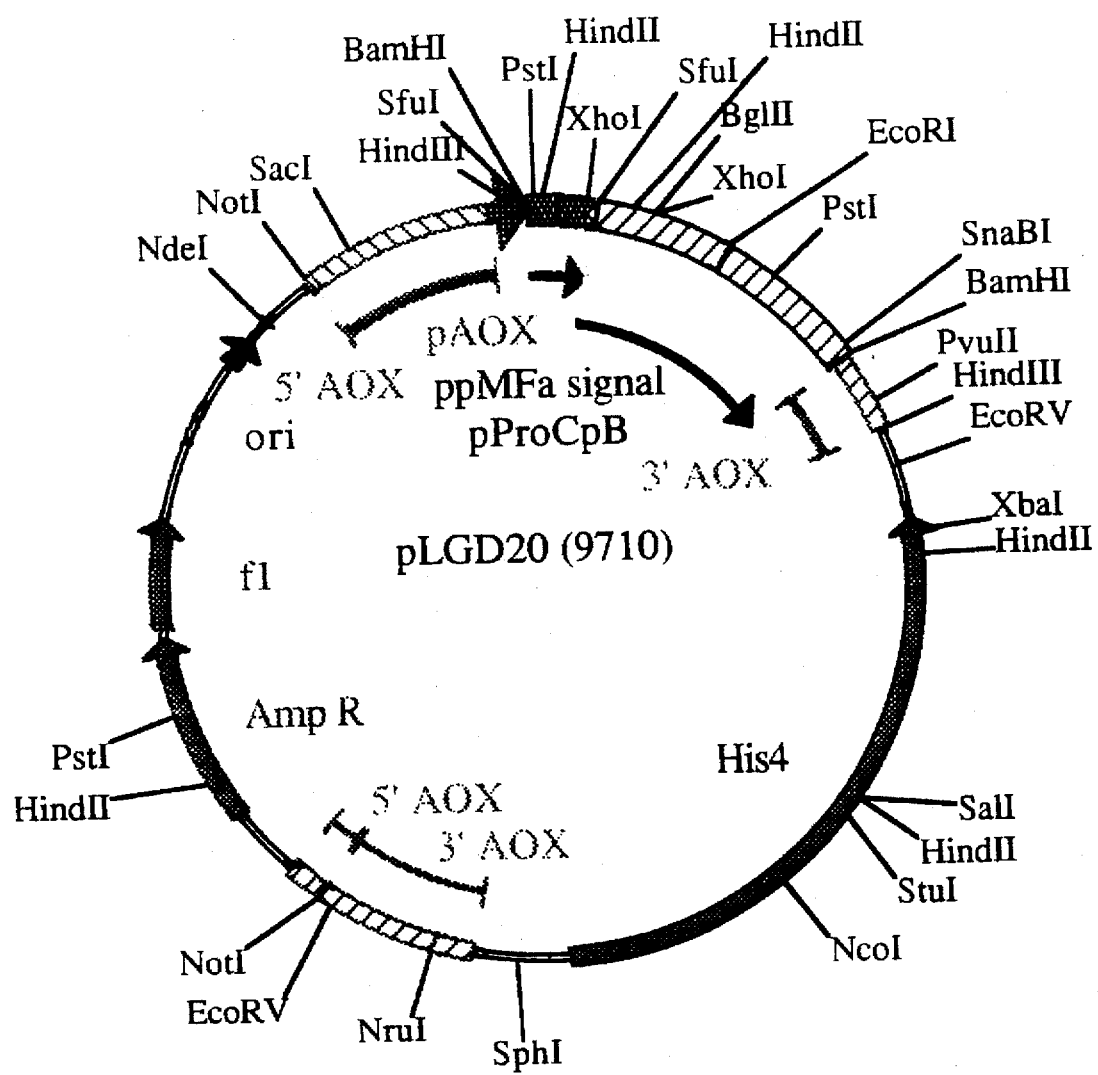
FIG. 9 is a restriction site and function map of plasmid pLGD20. pLGD20 contains approximately 9,710 base pairs.

A variety of promoters are operable in yeasts such as Pichia. The alcohol oxidase promoters (pAOX) are inducible with methanol. pAOX1 is available as a component of pLGD20, NRRL accession number B-21034. A restriction site and function map of pLGD20 is provided in FIG. 9. The glyceraldehyde-3-phosphate dehydrogenase promoter (pGAPDH or pGAP) has been deposited in the NRRL as a component of pLGD23 where it will be publicly available upon issuance of the present invention under the acession number B-21029. A restriction site and function map of pLGD23 is provided in FIG. 4. The phosphoglycerate kinase promoter (pPGK) is taught in U.S. Pat. No. 4,615,974, the contents of which are herein incorporated by reference.

Figure 2:
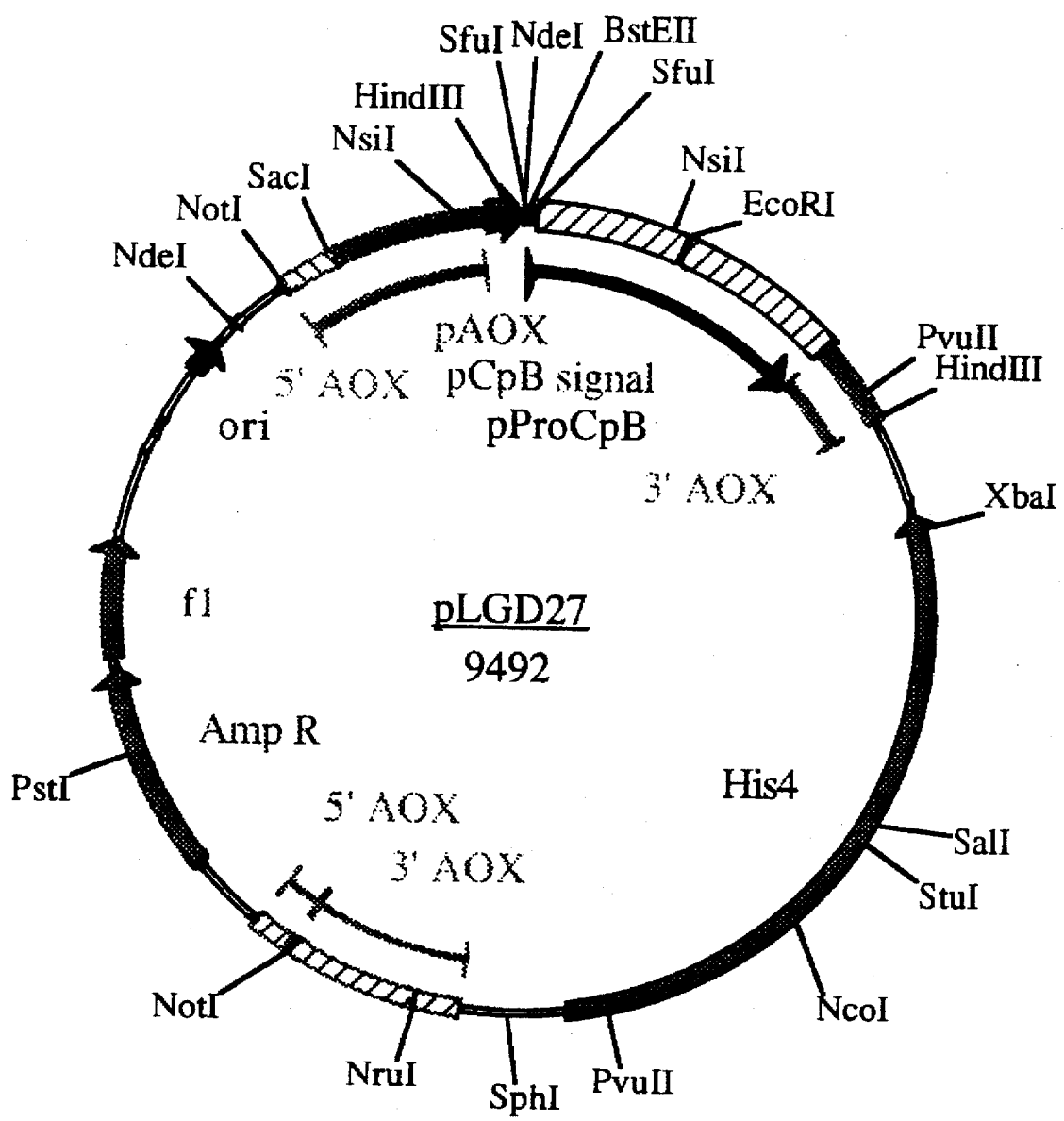
FIG. 2 is a restriction site and function map of plasmid pLGD27. pLGD27 contains approximately 9,492 base pairs.
Figure 3:
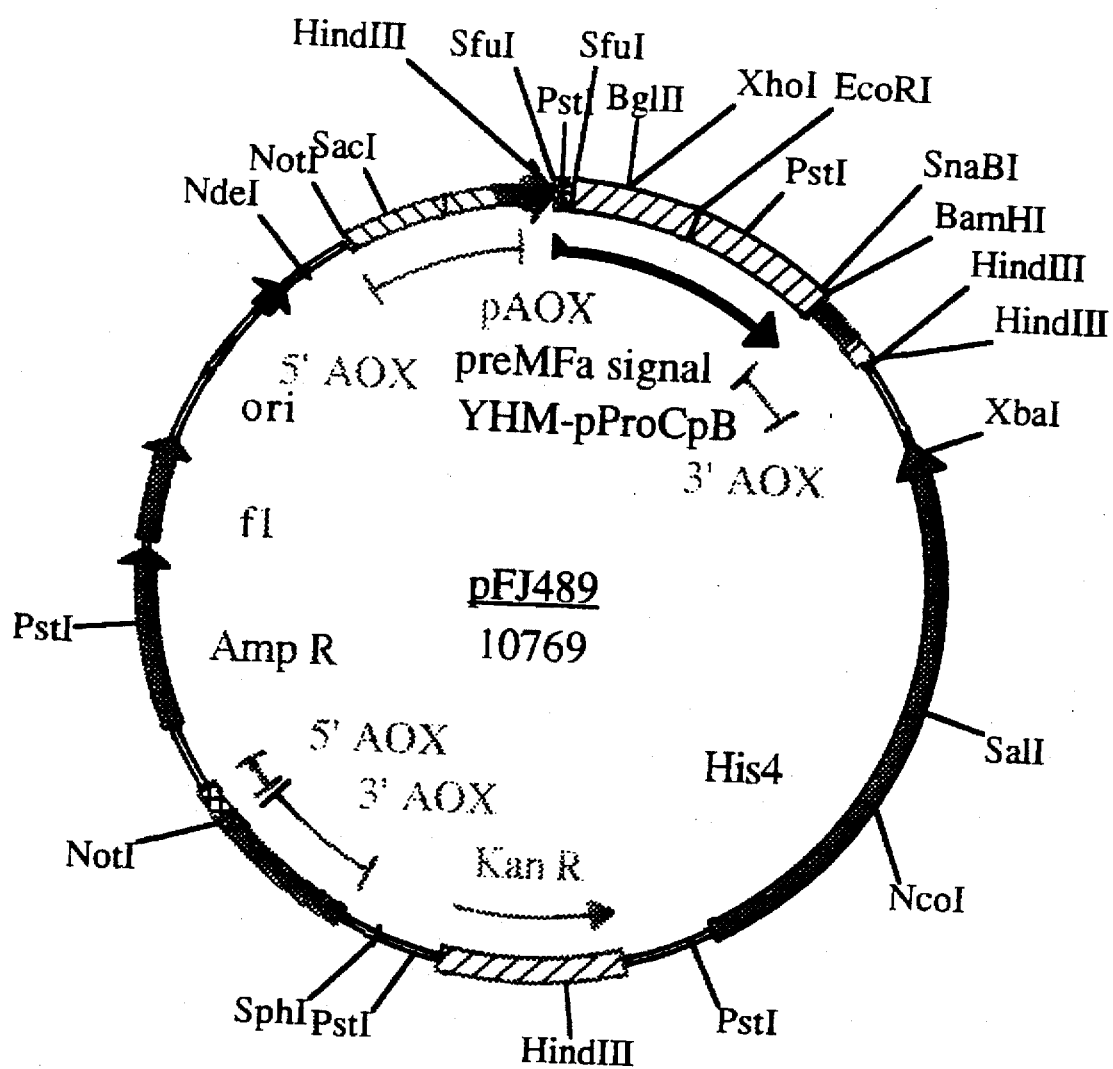
FIG. 3 is a restriction site and function map of plasmid pFJ489. pFJ489 contains approximately 10,769 base pairs.
Figure 6:
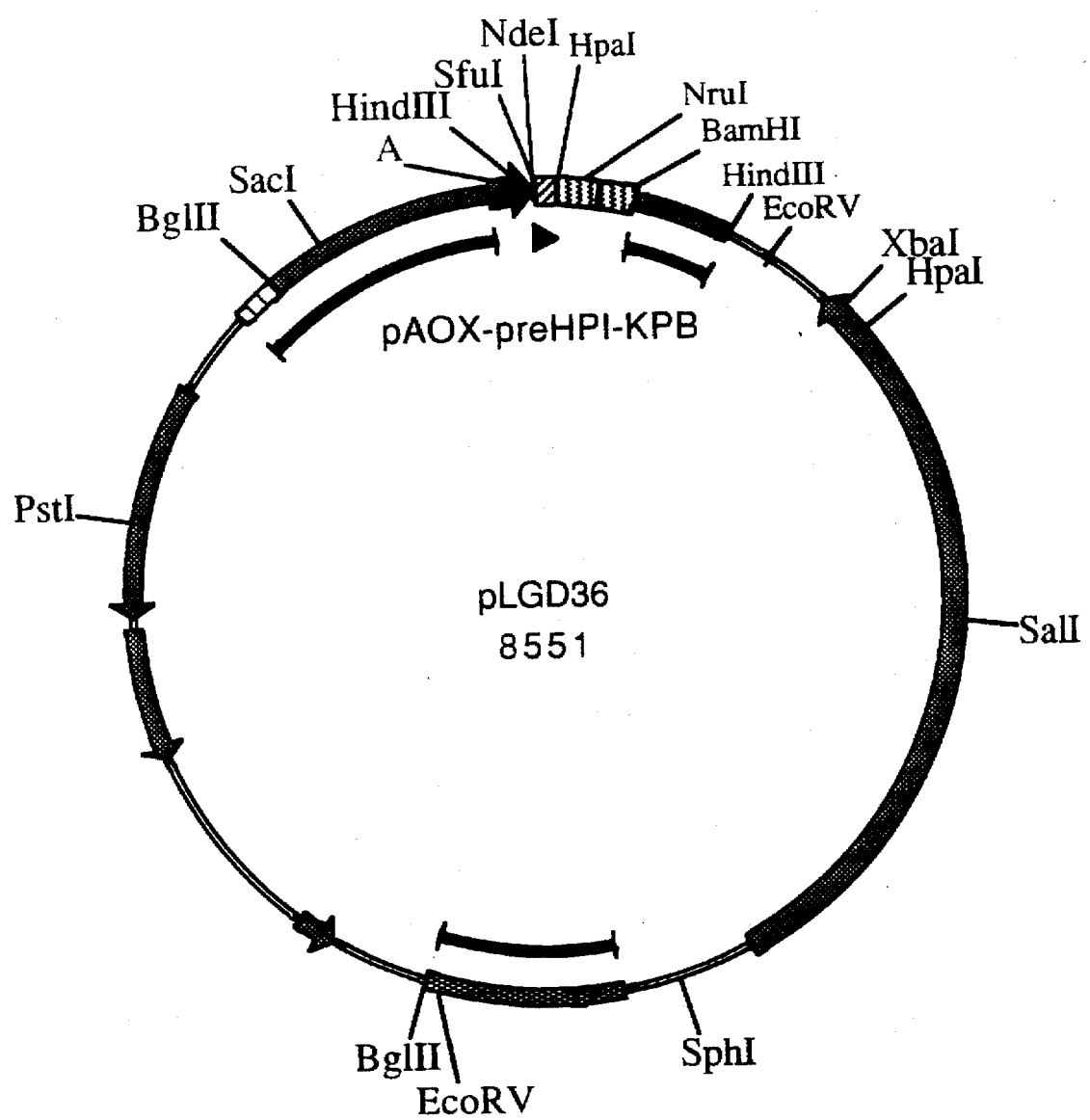
FIG. 6 is a restriction site and function map of plasmid pLGD36.
Figure 7:
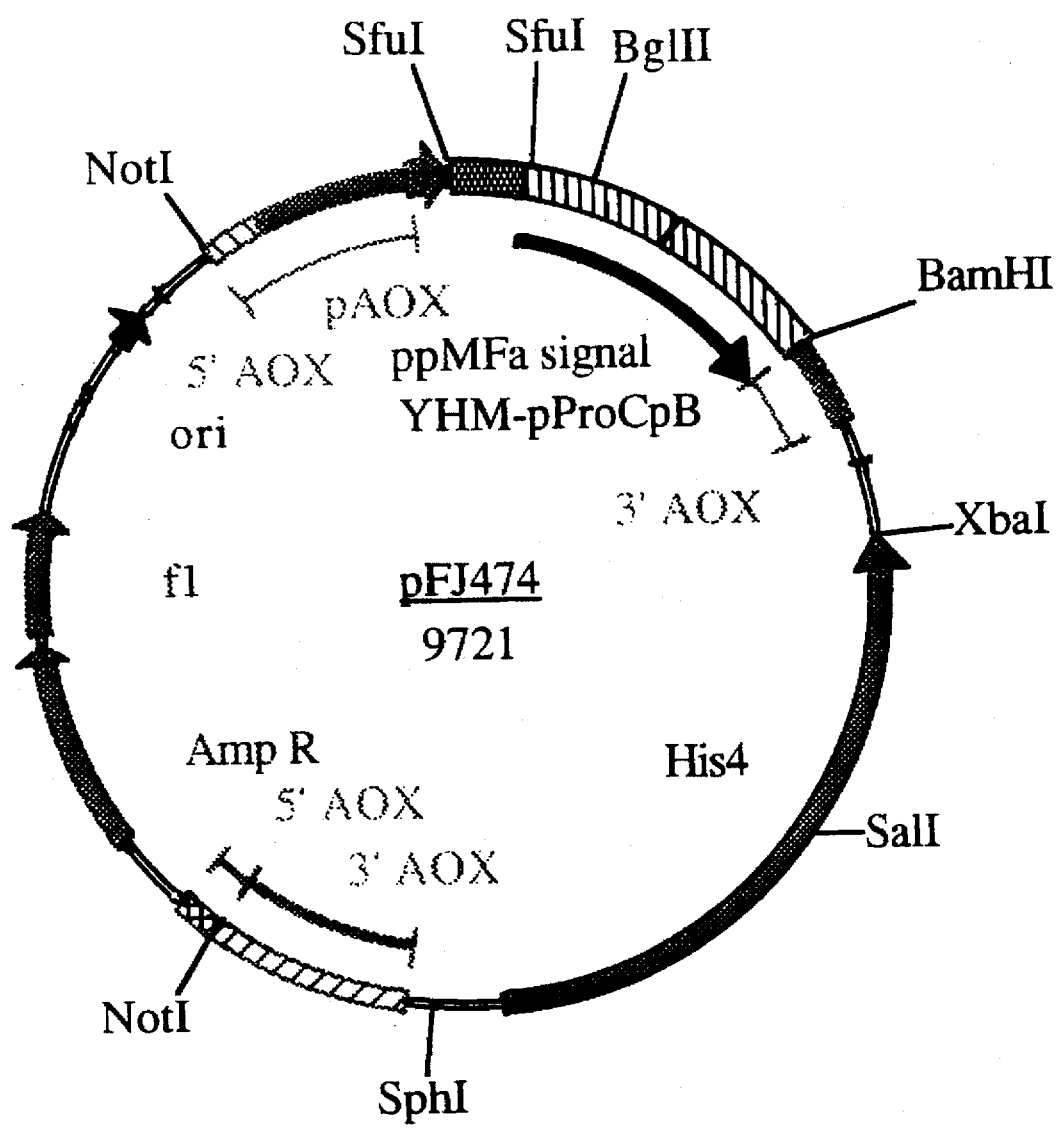
FIG. 7 is a restriction site and function map of plasmid pFJ474. pFJ474 contains approximately 9,721 base pairs.
Figure 8:
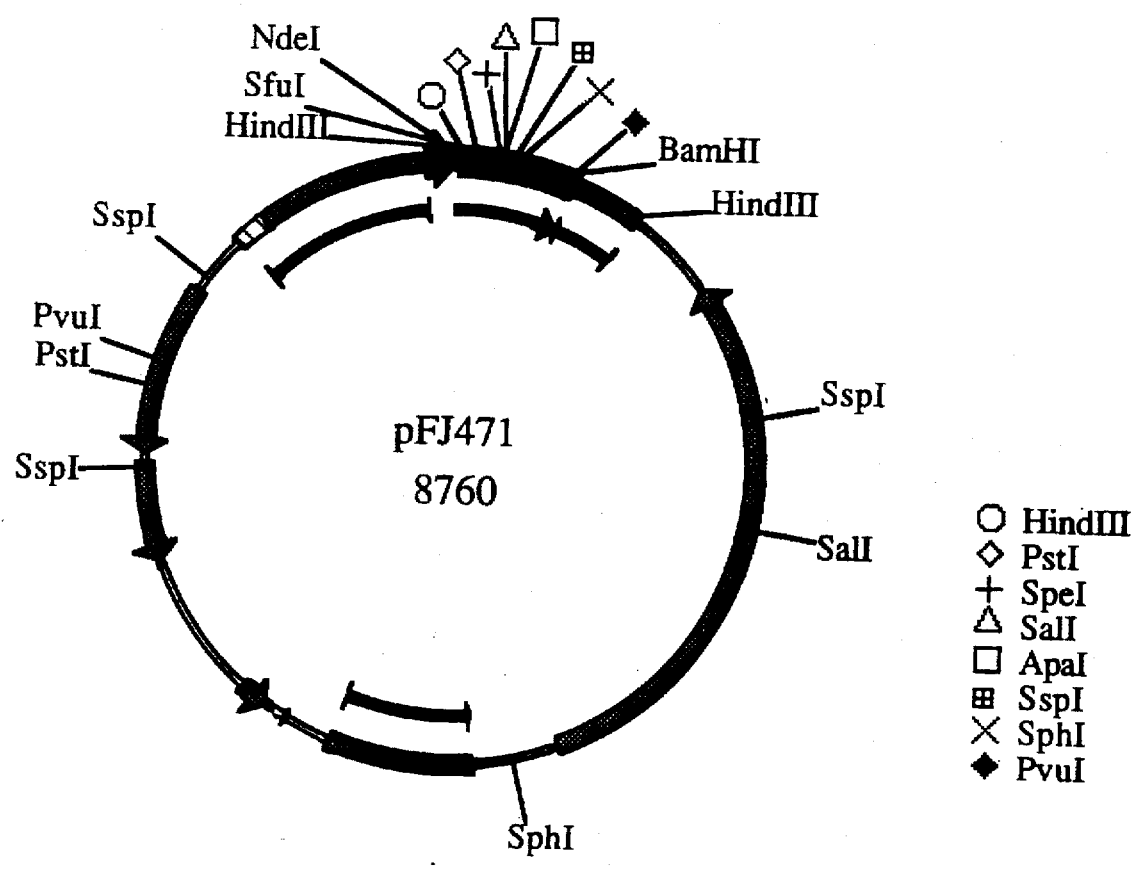
FIG. 8 is a restriction site and function map of plasmid pFJ471.

The preferred expression systems of the present invention include signal peptides (signals) for secretion of the desired product (porcine carboxypeptidase or an N-terminal extended equivalent thereof). Hitzeman et al., U.S. Pat. No. 4,775,622 teaches the expression, processing and secretion of heterologous proteins by yeast and thus provides an excellent discussion of the variety and utility of signals. Hitzeman et al., U.S. Pat. No. 4,775,622 is herein incorporated by reference. Chang et al., U.S. Pat. No. 5,010,003, teaches the use of yeast homologous signals to secrete heterologous proteins. The entire contents of U.S. Pat. No. 5,010,003 are herein incorporated by reference. Prepro-α mating factor is the preferred signal peptide. The plasmids pFJ474, NRRL B-21032, FIG. 7, and pLGD20, NRRL B-21034, FIG. 9 contain prepro-αmating factor signal. These vectors will be publicly available upon issuance of the present application and thus will provide a convenient source of the α mating factor signal sequence for construction of the other vectors of the present invention. The acid phosphatase signal peptide (PHO1) is well known in the art. The signal peptide for human serum albumin was deposited as a component of pLGD23 (NRRL B-21029, FIG. 4) and will be publicly available from the NRRL upon issuance of the present application. HPI is the abbreviation used in the Examples and Figures for the signal peptide for human proinsulin. HPI has been deposited as a component of pLGD36. pLGD36 (NRRL B-21031, FIG. 6) will be publicly available upon issuance of the present application. PreMFa, pre-α mating factor, is a component of plasmid pFJ489, which has been deposited in the NRRL under the accession number B-21028 where it will be publicly available upon issuance of the present application. FIG. 3 provides a restriction site and function map of plasmid pFJ489. CpB is the abbreviation used in the Examples and Figures for the signal peptide for porcine carboxypeptidase B. CpB can be conveniently prepared from plasmid pLGD27, NRRL B-21027, which will be publicly available upon issuance of the present application. A restriction site and function map of pLGD27 is provided in FIG. 2. TRPGEN is the designation used for the signal peptide for bovine trypsinogen. TRPGEN can be conveniently obtained from plasmid pFJ469, NRRL B-21025 which will become publicly available upon issuance of the present application. A restriction site and function map of plasmid pFJ489 is provided in FIG. 3. Plasmid pFJ471 comprises the signal peptide of human glucagon. Plasmid pFJ471 has been deposited in the NRRL where it will be publicly available under the accesssion number B-21033 upon issuance of the present application. A restriction site and function map of plasmid pFJ471 is provided in FIG. 8.

Pichia has endogenous enzymes which provide cleavage of the signal peptides. Kex2 processes after the second basic residue in sequences containing basic dipeptide units. Thus, appropriately exposed dipeptides containing any combination of arginine and/or lysine are cleaved by the Kex2 enzyme. The vectors of the present invention illustrate polypeptides which are cleaved by the Kex2 system. Constructs utilizing the ArgArg-HSA signal and the LysArg-MFα are provided and thus exemplify the use of Kex2 as a processing enzyme. The use of recombinant DNA to produce Kex2 in greater quantities is taught in U.S. Pat. No. 4,929,553, the contents of which are herein incorporated by reference.

Signal peptidase encoded by the SEC11 gene is well known in the art. The SEC11 gene product cleaves Ala-X-Ala, wherein X is any amino acid and is thus useful for removal of the "pre" region from constructs comprising the preMFA signal.

The Examples are preceded by a section of protocols which are common to many of the Examples. The protocols are provided with appropriate reference to the scientific and patent literature as a convenience to skilled artisans in their practice of the present invention.

Protocols

Protocol 1. Transformation of *Pichia pastoris* by electroporation.

100 ml of YPD media is innoculated with a loop of the desired *Pichia pastoris* strain which has been grown on an agar plate. YPD media is prepared by dissolving 10 grams of Bacto yeast extract, 20 grams of peptone in 900 ml of water (also include 20 grams of Bacto agar for YPD slants or plates) and autoclaving for 20 minutes and then adding 100 ml of sterile 20% (w/v) D-glucose. The YPD media, which has been innoculated with the appropriate *Pichia pastoris* strain, is incubated at 30° C. and a shaker bath for 48 hours. The *Pichia pastoris* is then subcultured by innoculation of 100 ml of YPD with samples of 10 µl, 30 µl, or 100 µl of the broth which is then incubated at 30° C. and the shaker bath overnight. An overnight culture having an optical density of between 0.8 and 1.5 (600 nm wavelength, blanked against media) is preferred. The culture having an appropriate optical density is then centrifuged to pellet the cells. The supernatant is decanted and 20 ml of cold sterile water is added to each tube. The cells are pelleted by centrifugal force. The pellet is then washed with an additional 20 ml of cold sterile water and centrifuged to collect the cells. After the centrifugation, 20 ml of cold 1M Sorbitol™ (Sigma) is added to each tube and the pellets are resuspended and transferred to a second tube. The culture is pelleted by centrifugation and 400 µl of cold 1M Sorbitol™ are added to the pellets. The pellets are resuspended by gently flicking the tubes and using a pipet tip to gently disassociate the pellets.

Approximately 10 µl of linear vector—prepared at a concentration of 1 µg/µl—is then added to 50 µl of the *Pichia pastoris* recipient strain prepared above. The DNA/*Pichia pastoris* preparations incubated on ice for 25 minutes, after which it is transferred to a cold 0.2 cm electroporation cuvette (BioRad). The electroporation mixture is then pulsed at 2.0 KV, 25 µF, 200 Ω using a BioRad Gene Pulsar System electroporation system. 500 µl of YPD media is added to the electroporation sample and the entire contents of this mixture is then transferred to a 5 ml centrifuge tube and incubated on ice until all samples have been pulsed for electroporation. The electroporation samples are then sampled to shaker bath at 30° C. and incubated for 30 minutes. The electroporation samples are then plated at volumes up to 100 µl onto MD plates. MD agar plates are prepared by mixing 100 ml of 10X YNB (6.7 grams of yeast nitrogen base without amino acids in 100 ml of water-filter sterilized), 2 ml of 500 X biotin (20 mg of biotin in 100 ml of water-filter sterilized) and 100 ml of 10X D-glucose with 800 ml of autoclaved water (include 15 grams Bacto agar for plates). The plates are then incubated at 30° C. for four days.

The HIS+ transformants are then patched to MD and YPD plates. The MD and YPD plates are incubated at 30° C. for 48 hours at which point colonies are readily discernible.

Protocol 2. Conventional transformation of *P. pastoris*

U.S. Pat. No. 5,166,329 teaches spheroplasting and conventional transformation protocols for *P. pastoris* at pages 9 and 10. The aforementioned teachings are herein incorporated by reference.

Protocol 3. Methanol induced expression of protein by *P. pastoris*

Methanol induction of transcription driven by alcohol oxidase promoters in *P. pastoris* is taught in U.S. Pat. No. 5,135,868, the contents of which are herein incorporated by reference.

EXAMPLE 1

Construction of pLGD43

Oligonucleotides DPG59 (Sequence I.D. 5) and DPG60 (Sequence I.D. 6) were synthesized, annealed and then phosphorylated. Oligonucleotide dry-pellets were resuspended in water (0.5 µg/µl) and then incubated for 15 minutes at 70° C. 20 µl of complimentary oligonucleotides, DPG59/60, were combined, incubated for 15 minutes at 70° C., and then cooled for 1 hour from 55° C. to room temperature (25° C.). 8.75 µg complementary oligonucleotide linker DNA was phosphorylated in 25 µl reaction containing 1 mM ATP (pH 8), 2.5 units polynucleotide kinase (New England Biolabs, hereinafter abbreviated NEB) and ligase buffer (Boehringer-Mannheim, hereinafter abbreviated BM) for 30 minutes at 37° C. Kinase was heat inactivated by a 10 minute incubation at 70° C.

10 µg of plasmid pLGD23 (NRRL B21029) was digested with 50 units of restriction enzyme NsiI in buffer H (BM). The reaction was incubated for 1 hour at 37° C. The 5'-termini phosphates were removed by adding 1 unit calf intestinal alkaline phosphatase, CIAP, and incubating for 30 minutes at 37° C. Enyzmes were heat inactivated by incubating for 10 minutes at 70° C.

0.35 µg DPG59/60 are combined with 0.1 µg NsiI-digested and dephosphorylated pLGD23. 1 unit T4 DNA ligase, ligase buffer (BM) and TE are added to a 15 µl final volume. The ligation reaction is incubated for 16 hours at 15° C. and then used to transform *E. coli* K12 MM294 cells. Transformants are selected on L-agar containing 50 µg/ml ampicillin. The sequence identity of desired vector pINT1 is confirmed by nucleotide sequencing.

20 µg pFJ474 (NRRL accession number B-21032, FIG. 7) was digested with 100 units restriction endonucleases NcoI and NruI in buffer B for 1 hour at 37° C. The 1.5 kb DNA fragment was gel-purified using 1% TBE agarose gel and DEAE paper.

20 µg of plasmid pINT1 is digested with 100 units restriction endonucleases SpeI and XbaI in buffer H (BM) for 1 hour at 37° C. The 5.6 kb DNA fragment containing the pPCpB gene was gel-purified using 1% agarose gel, Tris-borate buffer (TBE) and DEAE paper as described in *Molecular Cloning A Laboratory Manual*, Second Edition, Sambrook, J., Fritsch, I. and Maniatis, T., Cold Spring Harbor Press, Cold Spring Harbor, N.Y. (1989).

10 µg of plasmid pINT1 is digested with 50 units of restriction enzymes NcoI and NruI in buffer B (BM). The reaction is incubated for 1 hour at 37° C. DNA is precipitated by adding 0.1 vol 3M sodium acetate and 2.5 vol 100% EtOH. Lyophilyzed DNA is resuspended in a 100 µl reaction volume containing 50 units SpeI and XbaI, buffer H (BM) and TE (1.0 mM ethylenediamine tetraacetic acid in 0.01M (pH 7.4) Tris buffer) and then incubated for 1 hour at 37° C. The 5'-termini phosphates are removed by adding 1 unit calf intestine alkaline phosphatase (CIAP) and then incubating for 30 minutes at 37° C. Enyzmes are heat inactivated by incubating for 10 minutes at 70° C.

Approximately 0.5 µg of gel-purified plasmid pINT1 and 0.5 µg gel-purified pFJ474 DNA were combined with 0.1 µg plasmid pINT1 DNA which has been SpeI-, XbaI-, NruI-, and NcoI-digested and dephosphorylated as described above. 1 unit T4 DNA ligase, ligase buffer (BM) and TE were added to a 15 µl final volume. The ligation reaction was incubated for 16 hours at 15° C. and then used to transform *E. coli* K12 DH5α cells. Transformants are selected on L-agar containing 50 µg/ml ampicillin. Ampicillin-resistant transformants containing the desired pLGD43 construct were screened and identified by restriction enzyme analysis.

Formula 1

Sequence of Porcine Tyr—His—Met ProCarboxypeptidase B

```
                       N
                       d
                       e
                       I
TATCATATGCACCACTCCGGGGAGCATTTCGAAGGGGAGAAGGTGTTCCGTGTCAATGTT
   1 ---------+---------+---------+---------+---------+---------+
  60
            ATAGTATACGTGGTGAGGCCCCTCGTAAAGCTTCCCCTCTTCCACAAGGCACAGTTACAA
            Tyr His Met His His Ser Gly Glu His Phe Glu Gly Glu Lys Val Phe Arg Val Asn Val

GAAGATGAAAATGACATCAGCTTACTCCATGAGTTGGCCAGCACCAGGCAGATTGACTTC
  61 ---------+---------+---------+---------+---------+---------+
 120
            CTTCTACTTTTACTGTAGTCGAATGAGGTACTCAACCGGTCGTGGTCCGTCTAACTGAAG
            Glu Asp Glu Asn Asp Ile Ser Leu Leu His Glu Leu Ala Ser Thr Arg Gln Ile Asp Phe

TGGAAACCAGATTCTGTCACACAAATCAAACCTCACAGTACAGTTGACTTCCGTGTGAAA
 121 ---------+---------+---------+---------+---------+---------+
 180
            ACCTTTGGTCTAAGACAGTGTGTTTAGTTTGGAGTGTCATGTCAACTGAAGGCACACTTT
            Trp Lys Pro Asp Ser Val Thr Gln Ile Lys Pro His Ser Thr Val Asp Phe Arg Val Lys
```

Formula 1
Sequence of Porcine Tyr—His—Met ProCarboxypeptidase B

```
          GCAGAAGATATTTTGGCTGTGTGGAAGACTTTCTGGAGCAGAATGAACTACAATATGAGGTA
      181 ---------+---------+---------+---------+---------+---------+
      240
          CGTCTTCTATAAAACCGACACCTTCTGAAAGACCTCGTCTTACTTGATGTTATACTCCAT
          Ala Glu Asp Ile Leu Ala Val Glu Asp Phe Leu Glu Gln Asn Glu Leu Gln Tyr Glu Val

B
                              g           X
                              l           h
                              I           o
                              I           I
          CTCATAAACAACCTGAGATCTGTGCTCGAGGCTCAGTTTGACAGCAGAGTCCGTACAACT
      241 ---------+---------+---------+---------+---------+---------+
      300
          GAGTATTTGTTGGACTCTAGACACGAGCTCCGAGTCAAACTGTCGTCTCAGGCATGTTGA
          Leu Ile Asn Asn Leu Arg Ser Val Leu Glu Ala Gln Phe Asp Ser Arg Val Arg Thr Thr

GGACACAGTTATGAGAAGTACAACAACTGGGAAACGATCGAGGCTTGGACTAAGCAAGTC
      301 ---------+---------+---------+---------+---------+---------+
      360
          CCTGTGTCAATACTCTTCATGTTGTTGACCCTTTGCTAGCTCCGAACCTGATTCGTTCAG
          Gly His Ser Tyr Glu Lys Tyr Asn Asn Trp Glu Thr Ile Glu Ala Trp Thr Lys Gln Val

ACCAGTGAAAATCCAGACCTCATCTCTCGCACAGCCATCGGAACTACATTTTTAGGAAAC
      361 ---------+---------+---------+---------+---------+---------+
      420
          TGGTCACTTTTAGGTCTGGAGTAGAGAGCGTGTCGGTAGCCTTGATGTAAAAATCCTTTG
          Thr Ser Glu Asn Pro Asp Leu Ile Ser Arg Thr Ala Ile Gly Thr Thr Phe Leu Gly Asn

AATATATACCTCCTCAAGGTTGGCAAACCTGGACCAAATAAGCCTGCCATTTTCATGGAC
      421 ---------+---------+---------+---------+---------+---------+
      480
          TTATATATGGAGGAGTTCCAACCGTTTGGACCTGGTTTATTCGGACGGTAAAAGTACCTG
          Asn Ile Tyr Leu Leu Lys Val Gly Lys Pro Gly Pro Asn Lys Pro Ala Ile Phe Met Asp

TGTGGTTTCCATGCCAGAGAATGGATTTCCCATGCATTTTGCCAGTGGTTTGTGAGAGAG
      481 ---------+---------+---------+---------+---------+---------+
      540
          ACACCAAAGGTACGGTCTCTTACCTAAAGGGTACGTAAAACGGTCACCAAACACTCTCTC
          Cys Gly Phe His Ala Arg Glu Trp Ile Ser His Ala Phe Cys Gln Trp Phe Val Arg Glu

GCTGTTCTCACCTATGGATATGAGAGTCACATGACAGAATTCCTCAACAAGCTAGACTTT
      541 ---------+---------+---------+---------+---------+---------+
      600
          CGACAAGAGTGGATACCTATACTCTCAGTGTACTGTCTTAAGGAGTTGTTCGATCTGAAA
          Ala Val Leu Thr Tyr Gly Tyr Glu Ser His Met Thr Glu Phe Leu Asn Lys Leu Asp Phe

TATGTCTTGCCTGTGCTCAATATTGATGGCTACATCTACACCTGGACCAAGAACCGAATG
      601 ---------+---------+---------+---------+---------+---------+
      660
          ATACAGAACGGACACGAGTTATAACTACCGATGTAGATGTGGACCTGGTTCTTGGCTTAC
          Tyr Val Leu Pro Val Leu Asn Ile Asp Gly Tyr Ile Tyr Thr Trp Thr Lys Asn Arg Met

TGGAGAAAGACCCGCTCTACCAATGCTGGAACTACCTGCATTGGCACAGACCCCAACAGA
      661 ---------+---------+---------+---------+---------+---------+
      720
          ACCTCTTTCTGGGCGAGATGGTTACGACCTTGATGGACGTAACCGTGTCTGGGGTTGTCT
          Trp Arg Lys Thr Arg Ser Thr Asn Ala Gly Thr Thr Cys Ile Gly Thr Asp Pro Asn Arg

AATTTTGATGCTGGGTGGTGCACAACTGGAGCCTCTACAGACCCCTGCGATGAGACTTAC
      721 ---------+---------+---------+---------+---------+---------+
      780
          TTAAAACTACGACCCACCACGTGTTGACCTCGGAGATGTCTGGGGACGCTACTCGAAATG
          Asn Phe Asp Ala Gly Trp Cys Thr Thr Gly Ala Ser Thr Asp Pro Cys Asp Glu Thr Tyr
```

-continued
Formula 1
Sequence of Porcine Tyr—His—Met ProCarboxypeptidase B

```
                    P
                    s
                    t
                    I
        TGTGGATCTGCTGCAGAGTCTGAAAAAGAGACCAAGGCCCTGGCTGATTTTATACGCAAC
    781 ---------+---------+---------+---------+---------+---------+
    840
        ACACCTAGACGACGTCTCAGACTTTTTCTCTGGTTCCGGGACCGACTAAAATATGCGTTG
        Cys Gly Ser Ala Ala Glu Ser Glu Lys Glu Thr Lys Ala Leu Ala Asp Phe Ile Arg Asn

AACCTCTCCTCCATCAAAGCATACCTGACGATCCACTCATACTCACAGATGATACTCTAC
    841 ---------+---------+---------+---------+---------+---------+
    900
        TTGGAGAGGAGGTAGTTTCGTATGGACTGCTAGGTGAGTATGAGTGTCTACTATGAGATG
        Asn Leu Ser Ser Ile Lys Ala Tyr Leu Thr Ile His Ser Tyr Ser Gln Met Ile Leu Tyr

CCTTATTCCTATGATTACAAACTCCCCGAGAACAATGCTGAGTTGAATAACCTGGCTAAG
    901 ---------+---------+---------+---------+---------+---------+
    960
        GGAATAAGGATACTAATGTTTGAGGGGCTCTTGTTACGACTCAACTTATTGGACCGATTC
        Pro Tyr Ser Tyr Asp Tyr Lys Leu Pro Glu Asn Asn Ala Glu Leu Asn Asn Leu Ala Lys

GCTGCCGTGAAAGAACTTGCTACACTGTATGGCACCAAGTACACATACGGCCCAGGAGCT
    961 ---------+---------+---------+---------+---------+---------+
    1020
        CGACGGCACTTTCTTGAACGATGTGACATACCGTGGTTCATGTGTATGCCGGGTCCTCGA
        Ala Ala Val Lys Glu Leu Ala Thr Leu Tyr Gly Thr Lys Tyr Thr Tyr Gly Pro Gly Ala

ACAACAATCTATCCTGCTGCTGGGGGCTCTGATGACTGGGCTTATGACCAAGGAATCAAA
    1021 ---------+---------+---------+---------+---------+---------+
    1080
        TGTTGTTAGATAGGACGACGACCCCCGAGACTACTGACCCGAATACTGGTTCCTTAGTTT
        Thr Thr Ile Tyr Pro Ala Ala Gly Gly Ser Asp Asp Trp Ala Tyr Asp Gln Gly Ile Lys

TATTCCTTCACCTTTGAACTCCGGGATAAAGGCAGATATGGTTTTATCCTCCCTGAATCC
    1081 ---------+---------+---------+---------+---------+---------+
    1140
        ATAAGGAAGTGGAAACTTGAGGCCCTATTTCCGTCTATACCAAAATAGGAGGGACTTAGG
        Tyr Ser Phe Thr Phe Glu Leu Arg Asp Lys Gly Arg Tyr Gly Phe Ile Leu Pro Glu Ser

CAGATCCAGGCAACCTGTGAGGAAACAATGCTGGCCATCAAATACGTAACCAACTACGTG
    1141 ---------+---------+---------+---------+---------+---------+
    1200
        GTCTAGGTCCGTTGGACACTCCTTTGTTACGACCGGTAGTTTATGCATTGGTTGATGCAC
        Gln Ile Gln Ala Thr Cys Glu Glu Thr Met Leu Ala Ile Lys Tyr Val Thr Asn Tyr Val

CTGGGCCACCTGTAA
    1201 ---------+----- 1215
        GACCCGGTGGACATT
        Leu Gly His Leu End
```

---

We claim:

1. A DNA compound encoding porcine carboxypeptidase B, said DNA compound having the sequence of oligonucleotides of Sequence I.D. 3.

2. A recombinant DNA vector comprising the DNA compound of claim 1.

3. The vector of claim 2 that is a Pichia expression vector.

4. The vector of claim 2 that is a bacterial expression vector.

5. The Pichia expression vector of claim 3 that comprises a nucleotide sequence encoding the signal peptide of human serum albumin.

6. The Pichia expression vector comprising a nucleotide sequence encoding the signal peptide of human serum albumin of claim 5 that is plasmid pLGD23.

7. The Pichia expression vector of claim 3 that comprises a nucleotide sequence encoding the signal peptide of pre-mating factor α.

8. The Pichia expression vector of claim 3 that comprises a nucleotide sequence encoding the prepro-αmating factor signal peptide and propeptide.

9. The Pichia expression vector of claim 3 that comprises a nucleotide sequence encoding the porcine procarboxypeptidase B signal peptide.

10. The Pichia expression vector of claim 9 that is plasmid pLGD27.

11. A method for producing porcine carboxypeptidase B or an N terminal extended porcine carboxypeptidase B comprising the steps of:

(a) culturing the Pichia expression vector of claim 3;
    (b) recovering the carboxypeptidase B from the culture media and optionally cleaving the N terminal extension with trypsin.

12. A DNA compound encoding porcine carboxypeptidase B and the propeptide portion of porcine procarboxypeptidase B, said DNA compound characterized by having the sequence of nucleotides of SEQ ID NO:1.

13. A recombinant DNA Pichia expression vector that is plasmid pFJ489.

14. A recombinant DNA Pichia expression vector that is plasmid pFJ489.

* * * * *